(12) United States Patent
Liotta et al.

(10) Patent No.: US 8,507,673 B2
(45) Date of Patent: Aug. 13, 2013

(54) PROCESS FOR PREPARING 5,7 DIAMINOPYRAZOLO [1,5-A] PYRIMIDINE COMPOUNDS

(75) Inventors: Dennis C. Liotta, Atlanta, GA (US); James P. Snyder, Atlanta, GA (US); Ashutosh S. Jogalekar, Decatur, GA (US); Anthony G. M. Barrett, London (GB); Matthew John Fuchter, East Sussex (GB); Matthew J. Cook, Belfast (IE); Sebastian H. B. Kroll, Hertfordshire (GB)

(73) Assignees: Emory University, Atlanta, GA (US); Imperial College of Science and Technology, London (GB)

( * ) Notice: Subject to any disclaimer, the term of this patent is extended or adjusted under 35 U.S.C. 154(b) by 0 days.

(21) Appl. No.: 13/156,969

(22) Filed: Jun. 9, 2011

(65) Prior Publication Data
US 2012/0041198 A1    Feb. 16, 2012

Related U.S. Application Data

(63) Continuation of application No. PCT/US2009/067627, filed on Dec. 11, 2009.

(60) Provisional application No. 61/121,850, filed on Dec. 11, 2008.

(51) Int. Cl.
*C07D 487/04* (2006.01)

(52) U.S. Cl.
USPC ................. 544/281; 544/242; 544/253

(58) Field of Classification Search
USPC ................. 544/242, 253, 281
See application file for complete search history.

(56) References Cited

U.S. PATENT DOCUMENTS

| | | | | |
|---|---|---|---|---|
| 7,074,924 B2 * | 7/2006 | Guzi et al. | ............ | 544/281 |
| 7,119,200 B2 * | 10/2006 | Guzi et al. | ............ | 544/281 |
| 7,629,294 B2 * | 12/2009 | Gebauer et al. | ............ | 504/241 |
| 8,067,424 B2 * | 11/2011 | Jogalekar et al. | ............ | 514/259.3 |

FOREIGN PATENT DOCUMENTS

| | | |
|---|---|---|
| JP | 2006-160628 | 6/2006 |
| WO | WO 2005-077954 | 8/2005 |

OTHER PUBLICATIONS

International Search Report from PCT/US2009/067627, Oct. 14, 2010.

* cited by examiner

*Primary Examiner* — Golam M M Shameem
(74) *Attorney, Agent, or Firm* — King & Spalding

(57) ABSTRACT

Processes for the preparation of certain 5,7-diaminopyrazolo [1,5-α]pyrimidine compounds comprising the reaction of a primary or secondary amine and a protected 5-halo-7-aminopyrazolo[1,5-α]pyrimidine compound in solvent system comprising water and one or more organic solvents, optionally in the presence of an exogenous base.

13 Claims, No Drawings

PROCESS FOR PREPARING 5,7 DIAMINOPYRAZOLO [1,5-A] PYRIMIDINE COMPOUNDS

CROSS REFERENCE TO RELATED APPLICATION

This application is a continuation of International Application No. PCT/US2009/067627, filed 11 Dec. 2009, which claims priority to U.S. Provisional Patent Application No. 61/121,850, filed 11 Dec. 2008. The complete disclosure for each of the above-identified applications is hereby fully incorporated herein by reference.

FIELD OF THE INVENTION

This application relates to processes for preparing pyrazolo [1,5-α]pyrimidine compounds which have utility as pharmaceutically active compounds and as intermediates useful in the synthesis thereof. The compounds can be used to inhibit or modulate the activity of cyclin-dependent kinases, and are useful in the treatment of disease mediated by cyclin-dependent kinases.

BACKGROUND OF THE INVENTION

Cyclin-dependent kinases (CDKs) are the catalytic subunits of a large family of serine/threonine protein kinases. Activation of specific CDKs is required for the appropriate progression through a given stage of the cell cycle and into the next stage in the cell cycle. Regulation of CDK activity is pivotal for the correct timing of cell cycle progression and CDK activity is tightly regulated at many levels, including complex formation with cyclins and CDK inhibitors (CDKI), in particular CIP/KIP and INK-type CDKIs, as well as phosphorylation and dephosphorylation. Central to the activation of a given CDK is the requirement for association with cyclins and phosphorylation at a threonine residue in the activation loop (T-loop). Cyclins are synthesized and degraded during the cell cycle, so that activation of a particular CDK occurs only when its cyclin partner(s) becomes available. Additionally, many CDKs require phosphorylation of a threonine residue in the activation loop (T-loop) for their activation. In the case of CDK1, CDK2, CDK4 and CDK6 T-loop phosphorylation is mediated by the CDK activating kinase (CAK).

Deregulation of CDK activity forms an important part of many disease states, generally through elevated and/or inappropriate activation, as CDKs are infrequently mutated. Important mechanisms of CDK deregulation include cyclin overexpression. For example, the cyclin D1 gene is frequently amplified in cancer (Fu et al. *Endocrinology* 145: 5439-5447 (2004)). CDKI expression is frequently lost, for example, through mutational or epigenetic alterations in genes encoding INK4, CIP or KIP CDKIs in cancer (Malumbres and Barbacid, *Nature Reviews Cancer* 1, 223-231 (2001)).

CDKs are important targets for the design of drugs with antimimotic, antineurodegenerative, antiviral and antitumor effects. Recently, a class of CDK inhibitors having a pyrazolo [1,5-α]pyrimidine skeleton has been developed. These compounds show a high potency for inhibiting CDK2, and in some cases were shown to inhibit the growth of human colon tumor cells (D. S. Williamson et al., *Bioorg. Med. Chem. Lett.*, 15, 863-867 (2005)).

International Publication Nos. WO 04/022561 and WO 05/077954 to Guzi et al. describe certain pyrazolo[1,5-α] pyrimidine compounds which can be used as CDK inhibitors.

International Publication No. WO 08/027,220 to Chen et al. discloses processes for the preparation of certain (3-alkyl-5-piperidin-1-yl-3,3α-dihydro-pyrazolo [1,5-α]pyrimidin-7-yl)-amino derivatives which are described as useful as CDK inhibitors.

International Publication No. WO 08/151,304 to Emory University and Imperial College of Science and Technology describes certain pyrazolo[1,5-α]pyrimidine compounds for the inhibition of cyclin-dependent kinases and process of preparing these compounds using certain protecting groups and coupling catalysts at high temperatures.

There remains a need for improved processes for the preparation of amino-substituted pyrazolo[1,5-α]pyrimidine compounds that are useful as CDK inhibitors. In particular, a process suitable for large scale production of the compounds is needed. It is therefore an object of the invention to provide improved processes that allow large scale production of such compounds at low temperatures using ingredients that are available at reduced costs and with reduced toxicity.

SUMMARY OF THE INVENTION

The present application provides improved processes for the preparation of pyrazolo[1,5-α]pyrimidine compounds which circumvent the need for expensive and toxic catalysts and extreme conditions. Existing processes for preparation of 5,7-diaminopyrazolo[1,5-α]pyrimidine compounds are useful to prepare small amounts of the compounds, but these processes require caustic conditions such as catalyzed amination reactions or the use of high heat and extended reaction times to achieve amination at the 5 position. It has been discovered that amination of a protected 5-halo-7-aminopyrazolo[1,5-α]pyrimidine compound as described herein can be accomplished at low temperatures (less than 90° C.) in less than 24 hours and without the use of a transition metal catalyst.

Therefore, in one embodiment, a process is provided for preparation of a protected 5,7-diaminopyrazolo[1,5-α]pyrimidine compound comprising reacting a protected 5-halo-7-aminopyrazolo[1,5-α]pyrimidine compound, a primary or secondary amine, and a base in a solvent system comprising water and one or more organic solvents. This process is suitable for large scale synthesis as it can provide the products in high yields and purities while circumventing the need for any transition metal catalyzed reactions, high heat (100° C. or higher), or heating for more than 24 hours. In certain embodiments, the process additionally comprises deprotecting the protected 5,7-diaminopyrazolo[1,5-α]pyrimidine compound to produce a 5,7-diaminopyrazolo[1,5-α]pyrimidine compound that can be useful as a CDK inhibitor.

Scheme 3 lays out a specific embodiment of the invention:

Scheme 3

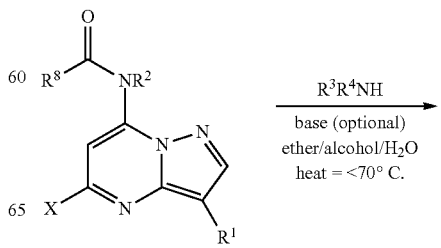

-continued

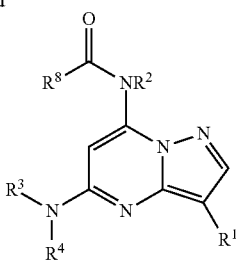

In certain alternate embodiments, a process is provided for preparing a protected 5,7-diaminopyrazolo[1,5-α]pyrimidine compound comprising reaction of an excess of primary or secondary amine and a protected 5-halo-7-aminopyrazolo[1,5-α]pyrimidine compound in a solvent system comprising water and one or more organic solvents in the absence of an exogenous base. In certain embodiments, the process additionally comprises deprotecting the protected 5,7-diaminopyrazolo[1,5-α]pyrimidine compound to produce a 5,7-diaminopyrazolo[1,5-α]pyrimidine compound that can be useful as a CDK inhibitor.

Scheme 4 lays out an alternate process of the invention.

Scheme 4

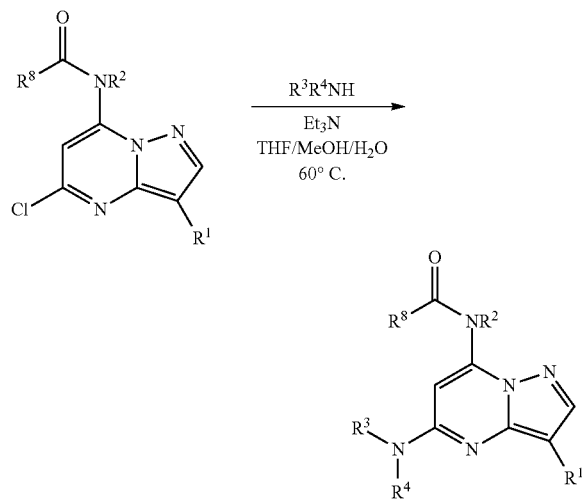

In a specific embodiment of the invention, a process is provided for preparing compounds of Formula I:

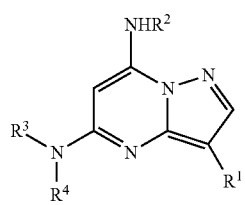

Formula I or salts thereof,
wherein
R$^1$ is H, halo, alkyl, haloalkyl, cycloalkyl, alkenyl, alkynyl, heterocyclyl, heterocyclylalkyl, aryl, aralkyl, heteroaryl, heteroaralkyl, amino, which may be substituted or unsubstituted;

R$^2$ is alkyl, haloalkyl, cycloalkyl, alkenyl, alkynyl, heterocyclyl, heterocyclylalkyl, aryl, aralkyl, heteroaryl, heteroaralkyl, amino, which may be substituted or unsubstituted;

R$^3$ is H, alkyl, aryl, cycloalkyl, which may be substituted or unsubstituted;

R$^4$ is alkyl, alkenyl, aryl, arylalkyl, arylalkenyl, cycloalkyl, heterocyclyl, heterocyclylalkyl, heteroaryl, and heteroarylalkyl; which may be substituted or unsubstituted;

comprising:
(a) reacting a compound of Formula II:

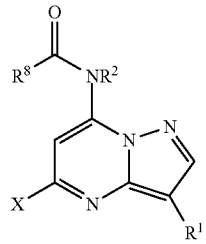

Formula II wherein
R$^8$ is C$_{1-8}$ alkyl, C$_{6-14}$ aryl, C$_{7-20}$ arylalkyl, C$_{4-7}$ heterocyclic, C$_{5-15}$ heterocyclicalkyl, C$_{4-7}$ heteroaryl, C$_{5-15}$ heteroaralkyl, C$_{1-8}$ alkoxy, C$_{6-14}$ aryloxy, C$_{7-20}$ arylalkoxy, C$_{4-7}$ heterocyclicoxy, C$_{5-15}$ heterocyclicalkoxy, C$_{4-7}$ heteroaryloxy, C$_{5-15}$ heteroaralkyloxy, all of which may be optionally substituted or unsubstituted;
X is F, Cl, Br, or I;
R$^1$ is as defined above; and
R$^2$ is as defined above and is, optionally, protected with a protecting group;
with a compound of Formula III:

R$^3$R$^4$NH    Formula III wherein
R$^3$ is as defined above and is, optionally, protected with a protecting group;
R$^4$ is as defined above and is, optionally, protected with a protecting group;
in a solvent system comprising water and one or more organic solvents, optionally in the presence of a base; and
(b) deprotecting the resulting compound to produce a compound of Formula I or a salt thereof.

In certain specific embodiments, the reaction is carried out at less than about 90° C., and more typically, less than about 85° C., less than about 80° C., less than about 75° C., less than about 70° C., less than about 65° C. or less than about 60° C. In certain embodiments, the reaction is carried out for less than 48 hours, or for less than about 36 hours, or for less than about 24 hours, or for less than about 12 hours and, in specific embodiments, the reaction is carried out for six hours, seven hours, eight hours, nine hours, ten hours or eleven hours. In one embodiment, the reaction proceeds to completion at 70° C. or less in 1 day or less.

In certain embodiments, the aqueous solvent system comprises an organic component. In more specific embodiments, the solvent system comprises an ether. In certain embodiments, the solvent system comprises an alcohol. Typically, the solvent system comprises an ether, an alcohol and water. In a particular embodiment, the solvent system comprises tetrahydrofuran (THF), methanol (MeOH) and water in a 1:1:1 ratio by volume. In another particular embodiment, the reaction comprises tetrahydrofuran (THF), methanol (MeOH), water and a base, for example triethylamine, in a 1:1:1:1 ratio by volume. In another particular embodiment, the reaction comprises tetrahydrofuran (THF), methanol (MeOH), water and an excess of the amine.

The primary or secondary amine can be a compound of Formula III: $R^3R^4NH$ wherein $R^3$ is H, alkyl, aryl, cycloalkyl, which may be substituted or unsubstituted, and optionally protected and $R^4$ is alkyl, alkenyl, aryl, arylalkyl, arylalkenyl, cycloalkyl, heterocyclyl, heterocyclylalkyl, heteroaryl, and heteroarylalkyl; which may be substituted or unsubstituted, and optionally protected. In more specific embodiments, the primary or secondary amine is a compound of Formula III wherein $R^3$ is H or $C_{1-5}$ alkyl substituted by 0-4 optionally protected substituents independently selected from OH, $NH_2$, or $NR_6R_7$ wherein $R_6$ and $R_7$ are each H or $C_{1-5}$ alkyl; and $R^4$ is $C_{1-8}$ alkyl substituted by 0-8 optionally protected substituents independently selected from OH, $NH_2$, or $NR_6R_7$ wherein $R_6$ and $R_7$ are each H or $C_{1-5}$ alkyl.

In a specific embodiment, a process for preparing 3-aminobutane-1,2,4-triol of Formula A or a diastereomer thereof is provided:

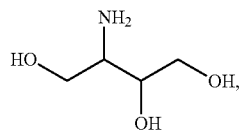
(A)

comprising (a) reacting a compound of Formula X:

(formula X)

wherein $R^a$ and $R^b$ are each independently $C_{1-5}$ alkyl with $SOCl_2$ and a base, (b) reacting the resulting compound with sodium azide, and (c) reducing the resulting compound to produce the 3-aminobutane-1,2,4-triol of Formula A or a diastereomer thereof. In certain embodiments, step (c) is reducing an ester groups of the resulting compound with a reducing agent and reducing an azido group on the resulting compound.

In certain embodiments, the compound of Formula A or diastereomer thereof is used in a process of preparation of a 5,7-diaminopyrazolo[1,5-α]pyrimidine compound wherein the process comprises reacting a compound of Formula A with a protected 5-halo-7-aminopyrazolo[1,5-α]pyrimidine compound in a solvent system comprising water and one or more organic solvents optionally in the presence of a base.

The processes described herein can be used to prepare compound of Formula I or salts thereof, for example compounds selected from the groups consisting of:

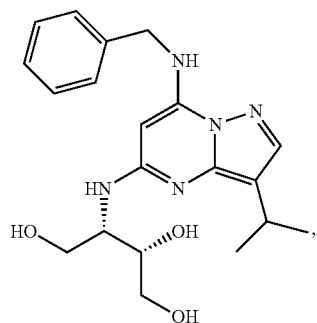
,

-continued

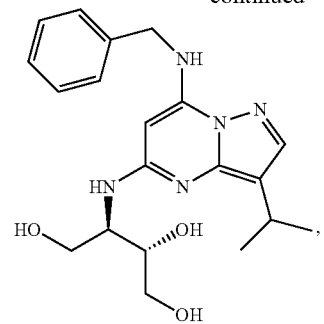
,

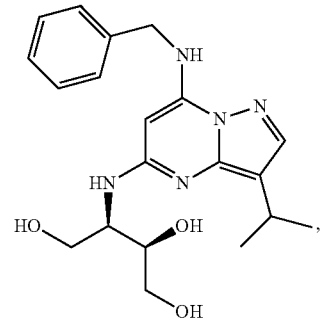
,

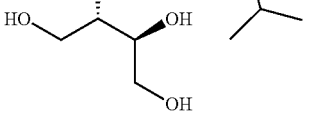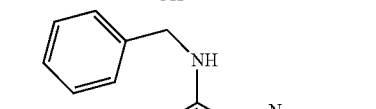, a mixture of diastereomers of

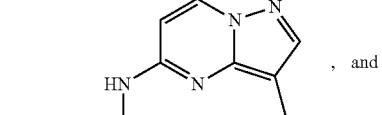, and

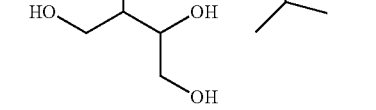

salts thereof.

DETAILED DESCRIPTION OF THE INVENTION

Preparation of 5,7-diaminopyrazolo[1,5-α]pyrimidine compounds such as those described herein and of International Publication No. WO 08/151,304 has been shown to proceed by amination of a 5,7-dihalo (and particularly dichloro)pyrazolo[1,5-α]pyrimidine compound. This reaction required two separate amination reactions, one to add an amine group at the 5 and the other to add an amine group at the 7 position of the pyrazolopyrimidine.

The numbering of the positions on the pyrazolo[1,5-α]pyrimidine compounds is shown in the structure below.

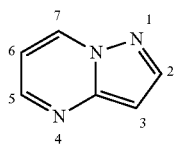

As previously described in International Publication No. WO 08/151,304, an amino group can be installed at the 7 position by the reaction an amine with a 5,7-dichloropyrazolo[1,5-α]pyrimidine compound (Scheme 1).

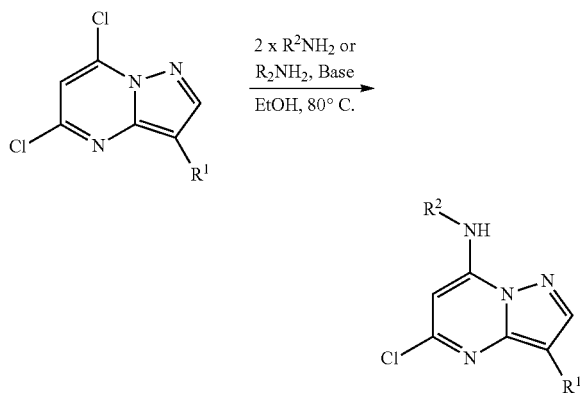

The resulting secondary amine from the C-7 amination reaction can be protected, for example as shown in Scheme 2.

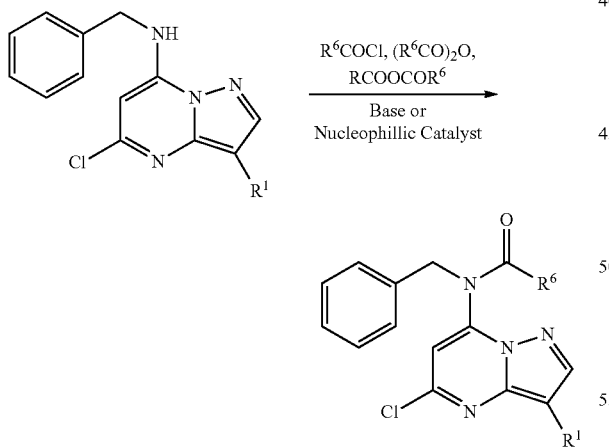

The second amino group is then installed at the 5 position of the 5-chloro-7-aminopyrazolo[1,5-α]pyrimidine compound. Existing processes for preparation of 5,7-diaminopyrazolo[1,5-α]pyrimidine compounds are useful to prepare small amounts of the compounds, but these processes require caustic conditions such as catalyzed amination reactions or the use of high heat and extended reaction times to achieve amination at the 5 position.

Processes of the Invention

It has now been discovered that the amination of the protected 5-halo-7-aminopyrazolo[1,5-α]pyrimidine compound can be accomplished at relatively low heat and without the use of a transition metal catalyst. The process typically occurs in the absence of a transition metal catalyst. This process comprises the reaction of a primary or secondary amine and a protected 5-halo-7-aminopyrazolo[1,5-α]pyrimidine compound in a solvent system, optionally including a base.

This reaction can typically be accomplished in less than one day at below 100° C., and in one embodiment, the reaction proceeds to completion at 70° C. or less in 1 day or less. In a particular embodiment, the solvent system comprises water and one or more organic solvents, and more typically, comprises an ether, an alcohol and water. In certain embodiments, the solvent system comprises tetrahydrofuran (THF), methanol (MeOH) and water in a 1:1:1 ratio by volume. In another particular embodiment, the reaction comprises tetrahydrofuran (THF), methanol (MeOH), water and a base, for example triethylamine, in a 1:1:1:1 ratio by volume. In another particular embodiment, the reaction comprises tetrahydrofuran (THF), methanol (MeOH), water and an excess of the amine. If an excess of the amine nucleophile is used no exogenous base is required.

Therefore, in one embodiment, a process is provided for preparation of a protected 5,7-diaminopyrazolo[1,5-α]pyrimidine compound comprising reacting a protected 5-halo-7-aminopyrazolo[1,5-α]pyrimidine compound, a primary or secondary amine, and a base in a solvent system comprising water and one or more organic solvents. This process is suitable for large scale synthesis as it can provide the products in high yields and purities while circumventing the need for any transition metal catalyzed reactions, high heat (100° C. or higher), or heating for more than 24 hours. In certain embodiments, the process additionally comprises deprotecting the protected 5,7-diaminopyrazolo[1,5-α]pyrimidine compound to produce a 5,7-diaminopyrazolo[1,5-α]pyrimidine compound that can be useful as a CDK inhibitor.

Scheme 3 lays out a specific embodiment of the invention:

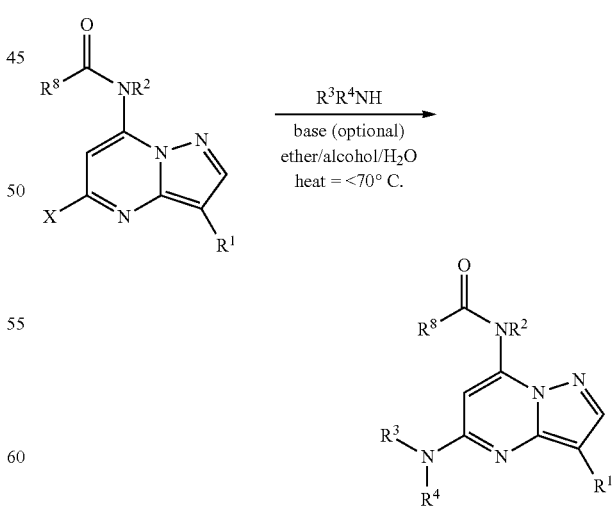

In certain alternate embodiments, a process is provided for preparing a protected 5,7-diaminopyrazolo[1,5-α]pyrimidine compound comprising reaction of an excess of primary or secondary amine and a protected 5-halo-7-aminopyrazolo

[1,5-α]pyrimidine compound in a solvent system comprising water and one or more organic solvents in the absence of an exogenous base. In certain embodiments, the process additionally comprises deprotecting the protected 5,7-diaminopyrazolo[1,5-α]pyrimidine compound to produce a 5,7-diaminopyrazolo[1,5-α]pyrimidine compound that can be useful as a CDK inhibitor.

Scheme 4 lays out an alternate process of the invention.

Scheme 4

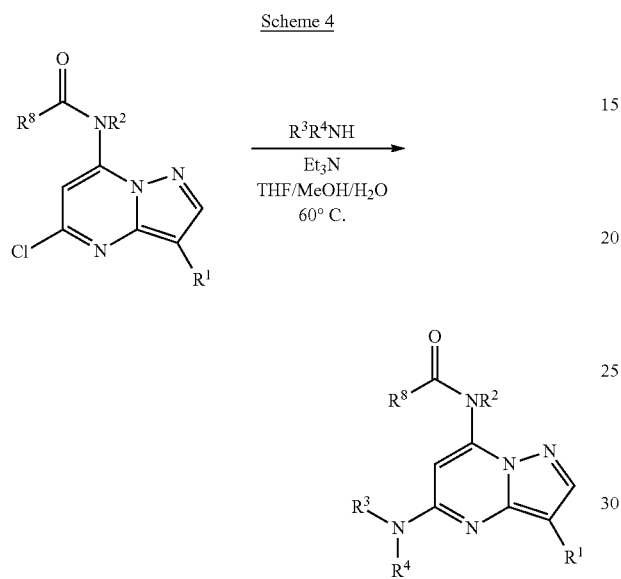

In a specific embodiment of the invention, a process is provided for preparing compounds of Formula I:

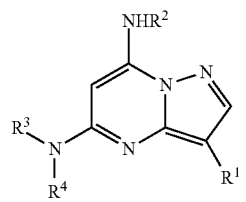

Formula I or salts thereof,
wherein
R¹ is H, halo, alkyl, haloalkyl, cycloalkyl, alkenyl, alkynyl, heterocyclyl, heterocyclylalkyl, aryl, aralkyl, heteroaryl, heteroaralkyl, amino, which may be substituted or unsubstituted;

R² is alkyl, haloalkyl, cycloalkyl, alkenyl, alkynyl, heterocyclyl, heterocyclylalkyl, aryl, aralkyl, heteroaryl, heteroaralkyl, amino, which may be substituted or unsubstituted;

R³ is H, alkyl, aryl, cycloalkyl, which may be substituted or unsubstituted;

R⁴ is alkyl, alkenyl, aryl, arylalkyl, arylalkenyl, cycloalkyl, heterocyclyl, heterocyclylalkyl, heteroaryl, and heteroarylalkyl; which may be substituted or unsubstituted;

comprising:

(a) reacting a compound of Formula II:

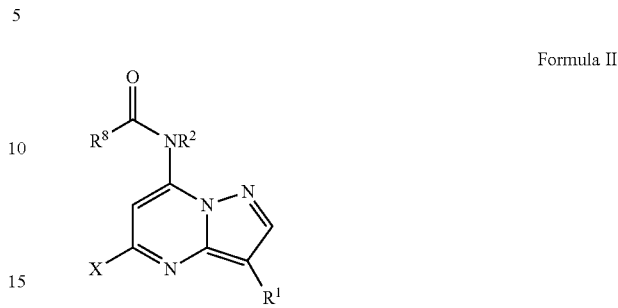

Formula II wherein

R⁸ is $C_{1-8}$ alkyl, $C_{6-14}$ aryl, $C_{7-20}$ arylalkyl, $C_{4-7}$ heterocyclic, $C_{5-15}$ heterocyclicalkyl, $C_{4-7}$ heteroaryl, $C_{5-15}$ heteroaralkyl, $C_{1-8}$ alkoxy, $C_{6-14}$ aryloxy, $C_{7-20}$ arylalkoxy, $C_{4-7}$ heterocyclicoxy, $C_{5-15}$ heterocyclicalkoxy, $C_{4-7}$ heteroaryloxy, $C_{5-15}$ heteroaralkyloxy, all of which may be optionally substituted or unsubstituted;

X is F, Cl, Br, or I;

R¹ is as defined above; and

R² is as defined above and is optionally protected with a protecting group;

with a compound of Formula III:

Formula III wherein

R³ is as defined above and is optionally protected with a protecting group;

R⁴ is as defined above and is optionally protected with a protecting group;

in a solvent system comprising water and one or more organic solvents, optionally in the presence of a base;

to produce a compound of Formula IV:

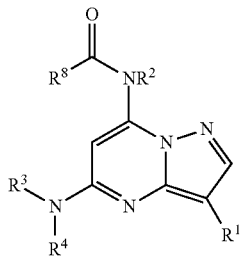

Formula IV wherein R², R³ and R⁴ are as defined above and are each, optionally, protected with a protecting group; and (b) deprotecting the compound of Formula IV to produce a compound of Formula I or a salt thereof.

In further embodiments, a process is provided for preparing compounds of Formula I:

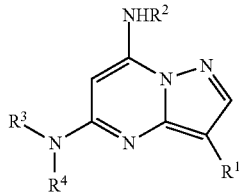

Formula I or salts thereof,
wherein
$R^1$ is H, $C_{1-5}$ alkyl or halo-substituted $C_{1-5}$ alkyl;
$R^2$ is substituted or unsubstituted $C_{1-8}$ alkyl, $C_{7-12}$ aralkyl, or $C_{5-20}$ heteroaralkyl;
$R^3$ is H or $C_{1-5}$ alkyl substituted by 0-4 substituents independently selected from OH, $NH_2$, or $NR_6R_7$ wherein $R_6$ and $R_7$ are each H or $C_{1-5}$ alkyl;
$R^4$ is $C_{1-8}$ alkyl substituted by 0-8 substituents independently selected from OH, $NH_2$, or $NR_6R_7$ wherein $R_6$ and $R_7$ are each H or $C_{1-5}$ alkyl;
comprising:
(a) reacting a compound of Formula II:

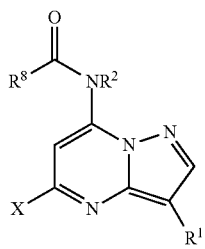

Formula II wherein
$R^8$ is $C_{1-8}$ alkyl, $C_{6-14}$ aryl, $C_{7-20}$ arylalkyl, $C_{4-7}$ heterocyclic, $C_{5-15}$ heterocyclicalkyl, $C_{4-7}$ heteroaryl, $C_{5-15}$ heteroaralkyl, $C_{1-8}$ alkoxy, $C_{6-14}$ aryloxy, $C_{7-20}$ arylalkoxy, $C_{4-7}$ heterocyclicoxy, $C_{5-15}$ heterocyclicalkoxy, $C_{4-7}$ heteroaryloxy, $C_{5-15}$ heteroaralkyloxy, all of which may be optionally substituted or unsubstituted;
X is F, Cl, Br, or I;
$R^1$ is H, $C_{1-5}$ alkyl or halo-substituted $C_{1-5}$ alkyl; and
$R^2$ is substituted or unsubstituted $C_{1-8}$ alkyl, $C_{7-12}$ aralkyl, or $C_{5-20}$ heteroaralkyl and is optionally protected with a protecting group;
with a compound of Formula III:

 $R^3R^4NH$           Formula III wherein
$R^3$ is H or $C_{1-5}$ alkyl substituted by 0-4 optionally protected substituents independently selected from OH, $NH_2$, or $NR_6R_7$ wherein $R_6$ and $R_7$ are each H or $C_{1-5}$ alkyl;
$R^4$ is $C_{1-8}$ alkyl substituted by 0-8 optionally protected substituents independently selected from OH, $NH_2$, or $NR_6R_7$ wherein $R_6$ and $R_7$ are each H or $C_{1-5}$ alkyl;

in a solvent system comprising water and one or more organic solvents, optionally in the presence of a base;
to produce a compound of Formula IV:

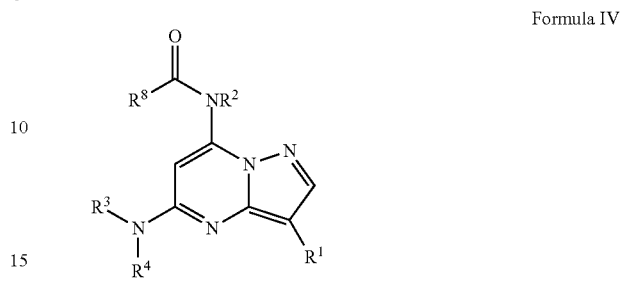

Formula IV wherein the substitutents on $R^2$, $R^3$ and $R^4$ are each, optionally, protected with a protecting group; and
(b) deprotecting the compound of Formula IV to produce a compound of Formula I or a salt thereof.

In certain embodiments, the process is carried out in a solvent system comprising water and one or more organic solvents, and more typically, in a solvent system comprising an ether, an alcohol and water. In certain embodiments, the process is carried out in a solvent system comprising water and two or more organic solvents.

In one embodiment, the process is a process for preparing compounds of Formula I or salts thereof wherein:
$R^1$ is $C_{1-5}$ alkyl or halo-substituted $C_{1-5}$ alkyl;
$R^2$ is substituted or unsubstituted $C_{5-7}$ alkyl, $C_{7-10}$ aralkyl, or $C_{5-11}$ heteroaralkyl;
$R^3$ is H or $C_{1-5}$ alkyl;
$R^4$ is $C_{1-6}$ alkyl substituted by 1-5 optionally protected substituents independently selected from OH, $NH_2$, or $NR_6R_7$ wherein $R_6$ and $R_7$ are each $C_{1-5}$ alkyl;
comprising:
(a) reacting a compound of Formula II wherein:
$R^8$ is $C_{1-8}$ alkyl, $C_{6-14}$ aryl, $C_{7-20}$ arylalkyl, $C_{1-8}$ alkoxy, $C_{6-14}$ aryloxy, $C_{7-20}$ arylalkoxy, all of which may be optionally substituted or unsubstituted; and
X is F, Cl, Br, or I;
$R^1$ is as defined above; and
$R^2$ is optionally protected substituted or unsubstituted $C_{5-7}$ alkyl, $C_{7-10}$ aralkyl, or $C_{5-11}$ heteroaralkyl;
with a compound of Formula III:

$R^3R^4NH$           Formula III wherein
$R^3$ is H or $C_{1-5}$ alkyl substituted by 0-4 protected $NH_2$ or protected OH groups;
$R^4$ is $C_{1-8}$ alkyl substituted by 0-4 protected $NH_2$ or protected OH groups;
and wherein there is at least one protected $NH_2$ or protected OH group on $R^3$ or $R^4$;
in a solvent system optionally in the presence of a base;
to produce a compound of Formula IV wherein the substitutents on $R^2$, $R^3$ and $R^4$ are optionally protected; and
(b) deprotecting the compound of Formula IV to produce a compound of Formula I or a salt thereof.

In another embodiment, the process is a process for preparing compounds of Formula I or salts thereof wherein:
$R^1$ is $C_{1-5}$ alkyl;
$R^2$ is substituted or unsusbstituted $C_{5-7}$ alkyl, $—(CH_2)_n$-phenyl, $—(CH_2)_n$-pyridyl, $—(CH_2)_n—$ furanyl, $—(CH_2)_n$-benzimidazolyl, or $—(CH_2)_n$-indolyl, wherein n is 1, 2, 3, or 4;

$R^3$ is H or $C_{1-5}$ alkyl;

$R^4$ is $C_{1-6}$ alkyl substituted by 1-5 optionally protected substituents independently selected from OH, $NH_2$, or $NR_6R_7$ wherein $R_6$ and $R_7$ are each $C_{1-5}$ alkyl;

comprising:

(a) reacting a compound of Formula II wherein:

$R^8$ is $C_{1-8}$ alkyl, $C_{6-14}$ aryl, $C_{7-20}$ arylalkyl, $C_{1-8}$ alkoxy, $C_{6-14}$ aryloxy, $C_{7-20}$ arylalkoxy, all of which may be optionally substituted or unsubstituted; and X is Cl or Br;

$R^1$ is as defined above; and $R^2$ is optionally protected substituted or unsusbstituted $C_{5-7}$ alkyl, $—(CH_2)_n$-phenyl, $—(CH_2)_n$-pyridyl, $—(CH_2)_n$-furanyl, $—(CH_2)_n$-benzimidazolyl, or $—(CH_2)_n$-indolyl;

with a compound of Formula III wherein:

$R^3$ is H or $C_{1-5}$ alkyl substituted by 0-4 protected $NH_2$ or protected OH groups;

$R^4$ is $C_{1-5}$ alkyl substituted by 0-4 protected $NH_2$ or protected OH groups; and wherein there is at least one protected $NH_2$ or protected OH group on $R^3$ or $R^4$;

in a solvent system optionally in the presence of a base;

to produce a compound of Formula IV; and (b) deprotecting the compound of Formula IV to produce a compound of Formula I or a salt thereof.

In one specific embodiment, a process is provided for preparing compounds of Formula V or salts or a diastereomer thereof:

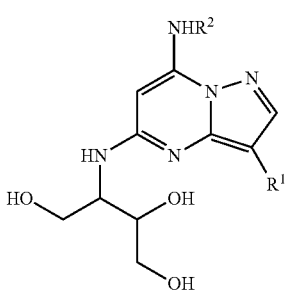

Formula V wherein:

$R^1$ is H, $C_{1-5}$ alkyl or halo-substituted $C_{1-5}$ alkyl;

$R^2$ is substituted or unsubstituted $C_{1-8}$ alkyl, $C_{7-12}$ aralkyl, or $C_{5-20}$ heteroaralkyl;

comprising:

(a) reacting a compound of Formula II:

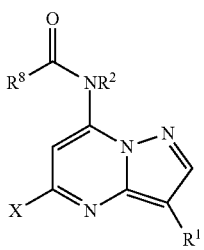

Formula II wherein $R^8$ is $C_{1-8}$ alkyl, $C_{6-14}$ aryl, $C_{7-20}$ arylalkyl, $C_{4-7}$ heterocyclic, $C_{5-15}$ heterocyclicalkyl, $C_{4-7}$ heteroaryl, $C_{5-15}$ heteroaralkyl, $C_{1-8}$ alkoxy, $C_{6-14}$ aryloxy, $C_{7-20}$ arylalkoxy, $C_{4-7}$ heterocyclicoxy, $C_{5-15}$ heterocyclicalkoxy, $C_{4-7}$ heteroaryloxy, $C_{5-15}$ heteroaralkyloxy, all of which may be optionally substituted or unsubstituted;

X is F, Cl, Br, or I;

$R^1$ is as defined above; and $R^2$ is as defined above and is optionally protected with a protecting group;

with a compound of Formula VI or a diastereomer thereof:

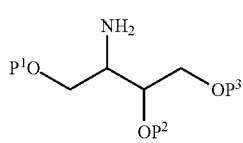

Formula VI wherein:

$P^1$, $P^2$ and $P^3$ are each a hydroxy protecting groups that is cleaved under acidic conditions;

in a solvent system comprising water and one or more organic solvents optionally in the presence of a base;

to produce a compound of Formula VII:

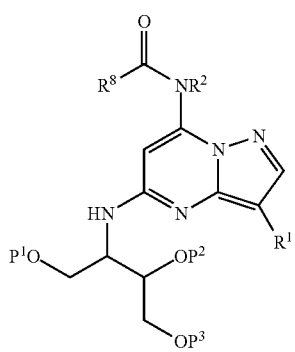

Formula VII wherein $R^2$ is optionally protected; and (b) deprotecting the compound of Formula VII to produce a compound of Formula V or a salt thereof.

In one embodiment, the compound of Formula VI:

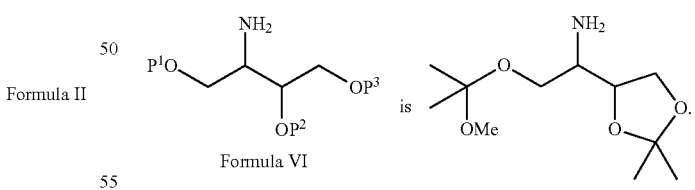

Formula VI

In one embodiment, the compound of Formula VI is a protected form of a the compound

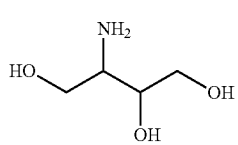

or a diastereomer thereof, which is prepared by the process comprising:

(i) reaction of a compound of the formula X:

   Formula X wherein $R^a$ and $R^b$ are each independently $C_{1-5}$ alkyl;
with $SOCl_2$ and a base to form a compound of Formula XI:

Formula XI

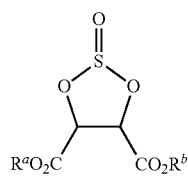

or a diastereomer thereof, (ii) addition of sodium azide to the compound of Formula XI to form an azido compound of Formula XII:

Formula XII

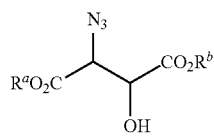

or a diastereomer thereof;

(iii) reduction of the ester groups of the compound of Formula XII with a reducing agent to form

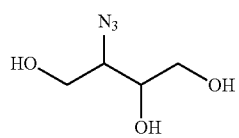

or a diastereomer thereof; and (iv) reduction of the azido group to produce 3-aminobutane-1,2,4-triol or a diastereomer thereof.

In one embodiment, the compound of Formula V is selected from the groups consisting of:

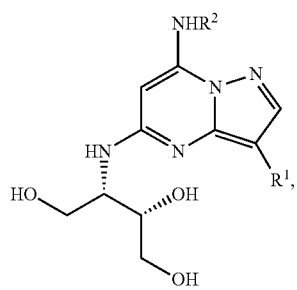

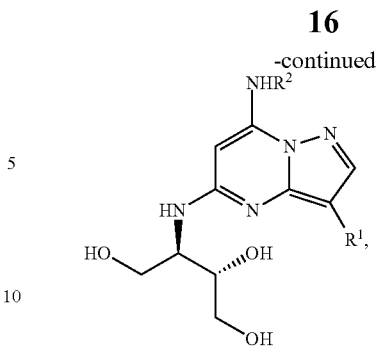

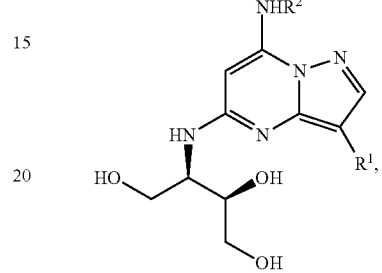

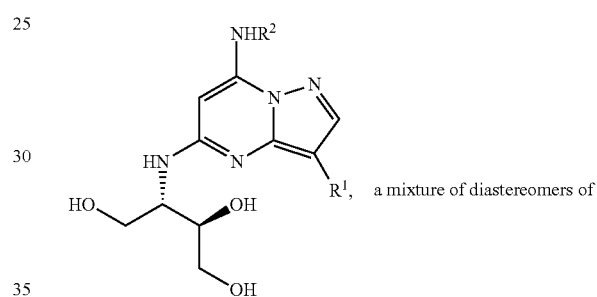

a mixture of diastereomers of

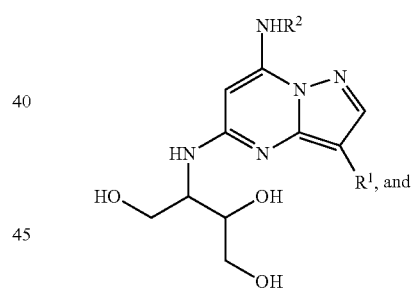

and salts thereof.

In one embodiment, the compound of Formula V is selected from the groups consisting of:

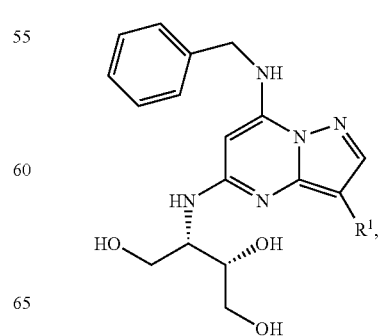

-continued
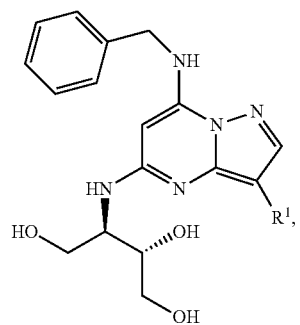
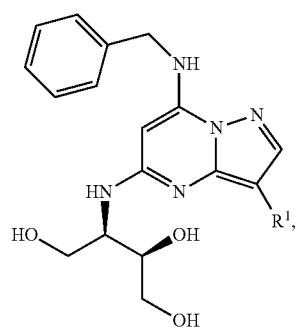
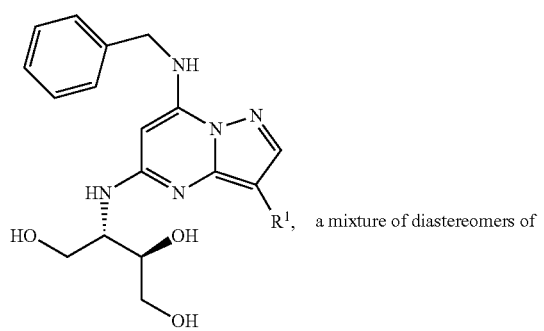, a mixture of diastereomers of
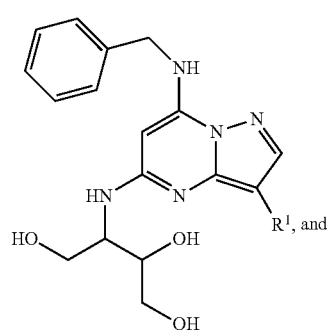
salts thereof.
In one embodiment, the compound of Formula V is selected from the groups consisting of:
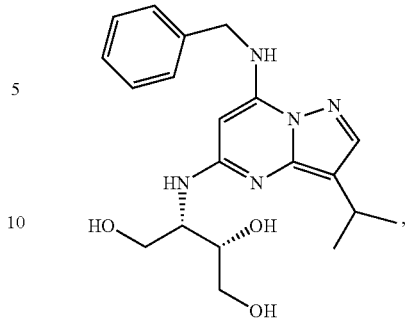
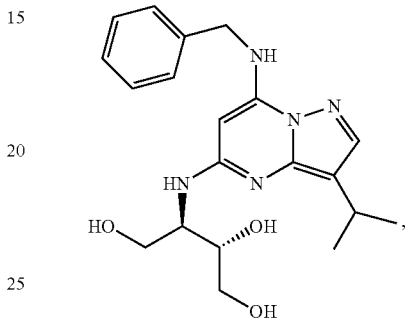
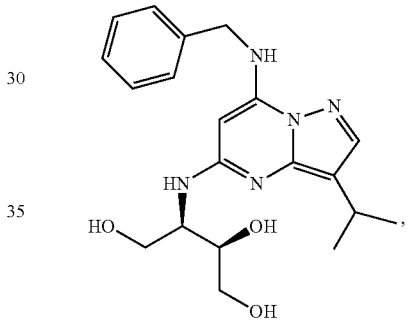
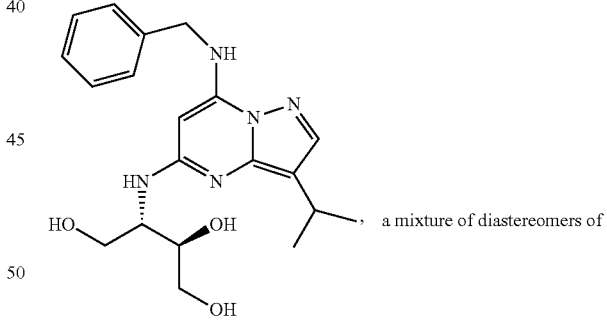, a mixture of diastereomers of
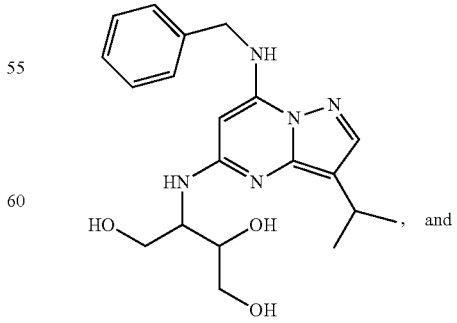, and
salts thereof.

In one embodiment of any of the foregoing processes, the process is for the preparation of the compound

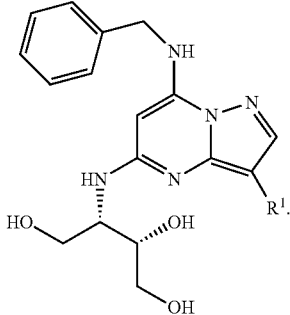

In one embodiment of any of the foregoing processes, the process is for the preparation of the compound

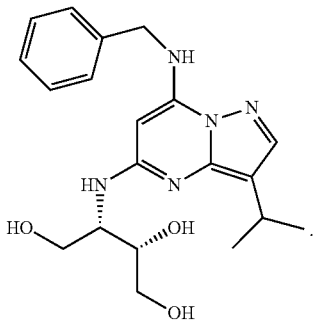 [SMILES: CC(C)c1cnn2c(NCc3ccccc3)cc(N[C@@H](CO)[C@H](O)CO)nc12]

In one embodiment of any of the foregoing processes, the process is for the preparation of the compound

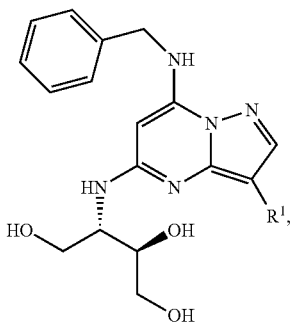

or a salt thereof.

In one embodiment of any of the foregoing processes, the process is for the preparation of the compound

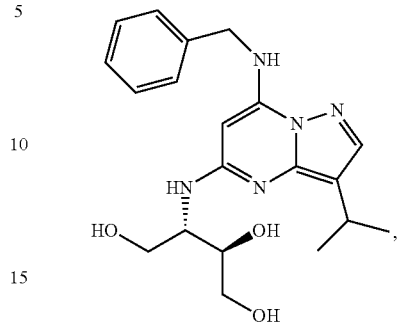

or a salt thereof.

In another embodiment, the compound of Formula I is selected from the group consisting of:

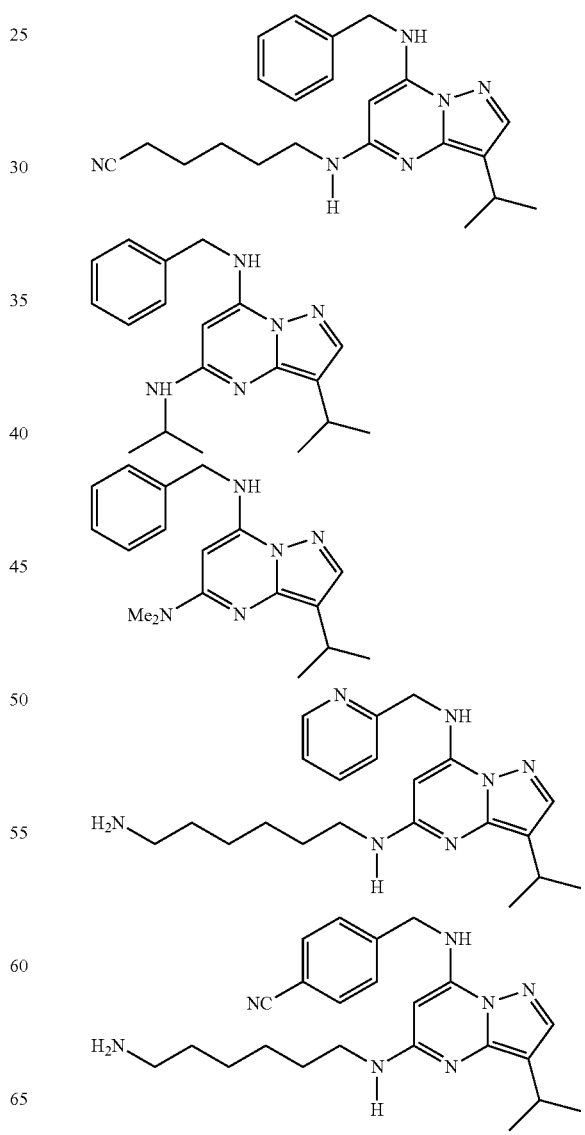

-continued

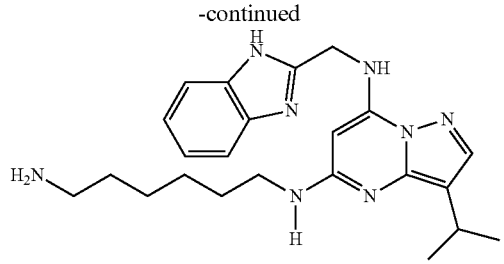

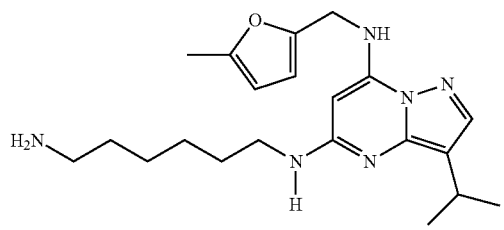

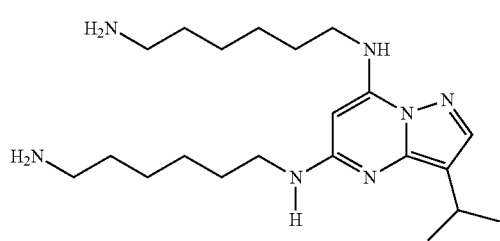

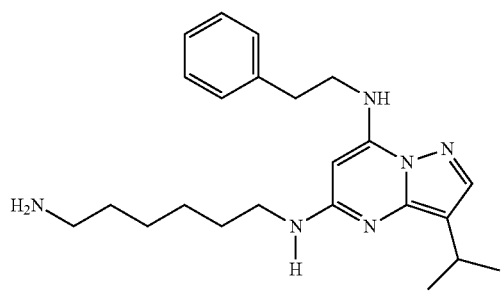

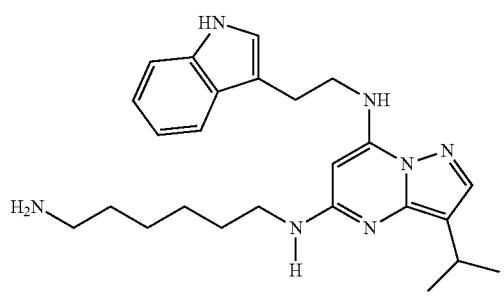

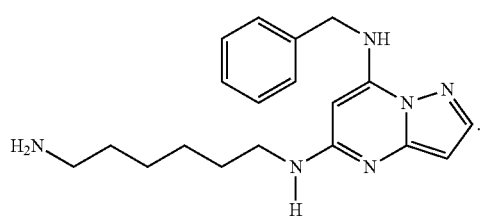

In a separate embodiment, a process is provided for preparing compounds of Formula V:

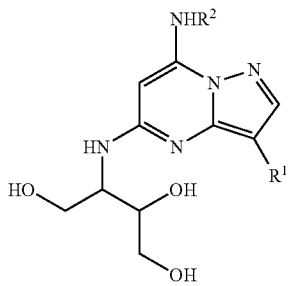

Formula V or salts or a diastereomer thereof, wherein
R$^1$ is H, C$_{1-5}$ alkyl or halo-substituted C$_{1-5}$ alkyl;
R$^2$ is substituted or unsubstituted C$_{1-8}$ alkyl, C$_{7-12}$ aralkyl, or C$_{5-20}$ heteroaralkyl;
comprising a cross coupling reaction of a compound of Formula II and an amine, for example a primary or secondary amine, in the presence of a catalyst. The cross coupling catalyst can be any cross coupling catalyst known in the art, for example, palladium, a palladium complex, a palladium salt optionally in the presence of ligands such as phosphine ligands. Typically, the palladium-catalyzed amination process is carried out in aprotic anhydrous solvent, for example toluene, in the presence of an appropriate base such as sodium tert-butoxide. The reaction mixture is usually subject to heating, for example to a temperature around 100° C.

In another embodiment, a process is provided for preparing compounds of Formula V:

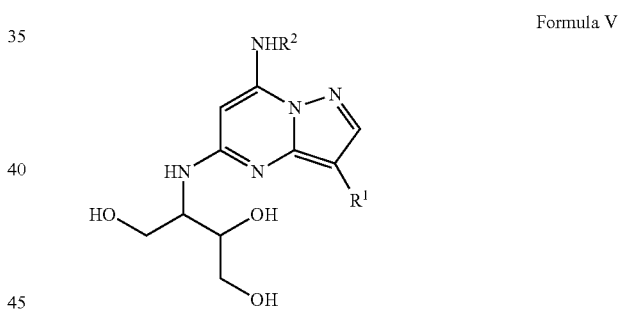

Formula V or salts or a diastereomer thereof,
wherein
R$^1$ is H, C$_{1-5}$ alkyl or halo-substituted C$_{1-5}$ alkyl;
R$^2$ is substituted or unsubstituted C$_{1-8}$ alkyl, C$_{7-12}$ aralkyl, or C$_{5-20}$ heteroaralkyl;
comprising:
reacting a compound of Formula II:

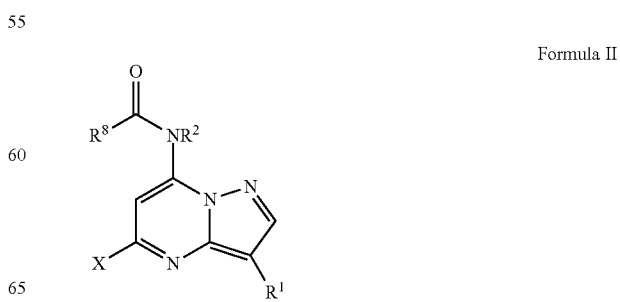

Formula II wherein
R⁸ is $C_{1-8}$ alkyl, $C_{6-14}$ aryl, $C_{7-20}$ arylalkyl, $C_{4-7}$ heterocyclic, $C_{5-15}$ heterocyclicalkyl, $C_{4-7}$ heteroaryl, $C_{5-15}$ heteroaralkyl, $C_{1-8}$ alkoxy, $C_{6-14}$ aryloxy, $C_{7-20}$ arylalkoxy, $C_{4-7}$ heterocyclicoxy, $C_{5-15}$ heterocyclicalkoxy, $C_{4-7}$ heteroaryloxy, $C_{5-15}$ heteroaralkyloxy, all of which may be optionally substituted or unsubstituted;
X is F, Cl, Br, or I;
$R^1$ is as defined above; and
$R^2$ is optionally protected substituted or unsubstituted $C_{1-8}$ alkyl, $C_{7-12}$ aralkyl, or $C_{5-20}$ heteroaralkyl;
with a compound of Formula VI:

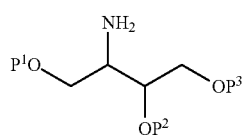

Formula VI or a diastereomer thereof;
wherein
$P^1$, $P^2$ and $P^3$ are each a hydroxy protecting groups that is cleaved under acidic conditions;
in the presence of a metal or metal complex; optionally in the presence of ligands;
optionally in the presence of a base;
in a solvent.

In one embodiment, the metal or metal complex is for example palladium. In a subembodiment, the reaction comprises ligands, for example phosphine ligands. In another embodiment, the reaction comprises a base, for example sodium tert-butoxide.

In another embodiment, the process further comprises deprotecting the product of the reaction.

Solvent System

A solvent system as described herein typically comprises at least water and one or more organic compound or organic solvents. In certain embodiments, the solvent system comprises water and two or more organic solvents. More typically, the solvent system comprises an ether, an alcohol and water. The solvent system can comprise an ether or mixture of ethers, an alcohol or mixture of alcohols, and water. In one embodiment, the solvent comprises tetrahydrofuran (THF), methanol (MeOH) and water. Typically, the solvent system does not comprise a metal catalyst.

An ether for use in the processes described herein is any compound which contains an ether group, or a compound of general formula R—O—R' which comprises an oxygen atom connected to two alkyl or aryl groups. Cyclic ethers may also be used. The ether may be any straight or branched dialkyl ether, alkylaryl ether or diaryl ether or heterocyclic ether, including but not limited to, THF, 1,4-dioxane, diethyl ether, dimethyl ether, diisopropyl ether, di-tert-butyl ether, dimethoxyethane, diethoxymethane, anisole, crown ethers and polyethylene glycol. In a particular embodiment, the ether is THF. In a particular embodiment, the ether is diisopropyl ether, di-tert-butyl ether, dimethoxyethane, or diethoxymethane. In a particular embodiment, the ether has a boiling point above 50° C. at ambient temperature and pressure. In a particular embodiment, the ether has a boiling point above 60° C. at ambient temperature and pressure. In a particular embodiment, a mixture of two, three or four ethers is used. In a particular embodiment, the ether is not 1,4-dioxane.

An alcohol for use in the processes described herein is any linear, branched or cyclic alkyl substituted by at least one hydroxy group including but not limited to methanol, ethanol, propanol, isopropanol, butanol, tert-butanol, isobutanol, pentanol, tert-amyl alcohol, hexanol, cyclohexanol, heptanol, and octanol. In a particular embodiment, the alcohol is methanol. In a particular embodiment, the alcohol is ethanol, propanol, isopropanol, butanol, tert-butanol, or isobutanol. In a particular embodiment, the alcohol has a boiling point above 50° C. at ambient temperature and pressure. In a particular embodiment, the alcohol has a boiling point above 60° C. at ambient temperature and pressure. In a particular embodiment, a mixture of two, three or four alcohols is used.

In one embodiment the ratio of the ether:alcohol:water mixture is in the range of about (1 to 3):(1 to 3):(1 to 3) by volume, for example about 1:1:1, about 2:1:1, about 3:1:1, about 1:2:1, about 1:1:2, about 2:2:1, about 2:1:2, about 1:2:2, about 1:3:1, about 1:1:3, about 1:3:3, about 3:3:1, about 3:1:3, about 2:2:3, about 2:3:2, or about 3:2:2, by volume. In a particular embodiment, the ratio of the ether:alcohol:water mixture is about 1:1:1 by volume.

In a particular embodiment, the ether or mixture of ethers in the ether:alcohol:water mixture comprises at least 10%, at least 20%, at least 25%, at least 30%, at least 35%, at least 40%, at least 45%, at least 50% or at least 60% of the ether:alcohol:water mixture. In another embodiment, the ether or mixture of ethers comprises about 10% to about 60%, about 20% to about 60%, about 20% to about 50%, about 20% to about 40%, about 25% to about 40%, about 25% to about 35% of the solvent mixture or ether:alcohol:water mixture by volume. In a particular embodiment, the ether or mixture of ethers comprises about 25% to about 35% of the solvent mixture or ether:alcohol:water mixture by volume, for example about 25%, 26%, 27%, 28%, 29%, 30%, 31%, 32%, 33%, 34% or 35% of the mixture.

In a particular embodiment, the alcohol or mixture of alcohols in the ether:alcohol:water mixture comprises at least 10%, at least 20%, at least 25%, at least 30%, at least 35%, at least 40%, at least 45%, at least 50% or at least 60% of the ether:alcohol:water mixture. In another embodiment, the alcohol or mixture of alcohols comprises about 10% to about 60%, about 20% to about 60%, about 20% to about 50%, about 20% to about 40%, about 25% to about 40%, about 25% to about 35% of the solvent mixture or ether:alcohol:water mixture by volume. In a particular embodiment, the alcohol or mixture of alcohols comprises about 25% to about 35% of the solvent mixture or ether:alcohol:water mixture by volume, for example about 25%, 26%, 27%, 28%, 29%, 30%, 31%, 32%, 33%, 34% or 35% of the mixture.

In a particular embodiment, the water in the ether:alcohol:water mixture comprises at least 10%, at least 20%, at least 25%, at least 30%, at least 35%, at least 40%, at least 45%, at least 50% or at least 60% of the ether:alcohol:water mixture. In another embodiment, the water comprises about 10% to about 60%, about 20% to about 60%, about 20% to about 50%, about 20% to about 40%, about 25% to about 40%, about 25% to about 35% of the solvent mixture or ether:alcohol:water mixture by volume. In a particular embodiment, the water comprises about 25% to about 35% of the solvent mixture or ether:alcohol:water mixture by volume, for example about 25%, 26%, 27%, 28%, 29%, 30%, 31%, 32%, 33%, 34% or 35% of the mixture.

In a subembodiment, the ether:alcohol:water mixture comprises about 25% to about 35% ether, about 25% to about 35% alcohol, and about 25% to about 35% water, by volume and in any combination such the total of the ether, alcohol and water components is 100%.

Base Reactions

In one embodiment, step (a) of the processes described herein, or the reaction of a compound of Formula II with a compound of Formula III, is conducted in the absence of an exogeneous or additional base. In a particular embodiment, an excess, or greater than stoichiometric amount, of a compound of Formula III is used in step (a).

In one embodiment, step (a) of the processes described herein, or the reaction of a compound of Formula II with a compound of Formula III, is conducted in the presence of a base. The base may be an amine, for example a tertiary amine or trialkylamine, such as trimethylamine, triethylamine or diisopropylethylamine. The base can also be dimethylethanolamine, pyridine, 4-methylmorpholine, 1,8-diazabicyclo[5,4,0]-7-undecene (DBU) and the like. In one embodiment, the base is triethylamine ($Et_3N$). In another embodiment, the base is diisopropylethylamine. In another embodiment, the base is not diisopropylethylamine. In one embodiment, the base is not N-methylpyrrollidine.

In one embodiment the ratio of the ether:alcohol:water:base mixture is in the range of about (1 to 3):(1 to 3):(1 to 3):(1 to 3), for example about 1:1:1:1, 1:1:1:2, 1:1:2:1, 1:2:1:1, 2:1:1:1, 1:1:2:2, 1:2:2:1, 2:2:1:1, 2:1:2:1, 1:2:1:2, or 2:1:1:2, by volume. In a particular embodiment, the ratio of the ether:alcohol:water:base mixture is about 1:1:1:1 by volume.

In a particular embodiment, the ether or mixture of ethers in the ether:alcohol:water:base mixture comprises at least 10%, at least 15%, at least 20%, at least 25%, at least 30%, at least 35%, at least 40%, at least 45%, at least 50% or at least 60% of the ether:alcohol:water:base mixture. In another embodiment, the ether or mixture of ethers comprises about 10% to about 60%, about 15% to about 50%, about 20% to about 50%, about 15% to about 40%, about 15% to about 35%, about 20% to about 30% of the solvent mixture or ether:alcohol:water:base mixture by volume. In a particular embodiment, the ether or mixture of ethers comprises about 20% to about 30% of the solvent mixture or ether:alcohol:water:base mixture by volume, for example about 20%, 21%, 22%, 23%, 24%, 25%, 26%, 27%, 28%, 29%, or 30% of the mixture.

In a particular embodiment, the alcohol or mixture of alcohols in the ether:alcohol:water:base mixture comprises at least 10%, at least 15%, at least 20%, at least 25%, at least 30%, at least 35%, at least 40%, at least 45%, at least 50% or at least 60% of the ether:alcohol:water:base mixture. In another embodiment, the alcohol or mixture of alcohols comprises about 10% to about 60%, about 15% to about 50%, about 20% to about 50%, about 15% to about 40%, about 15% to about 35%, about 20% to about 30% of the solvent mixture or ether:alcohol:water:base mixture by volume. In a particular embodiment, the alcohol or mixture of alcohols comprises about 20% to about 30% of the solvent mixture or ether:alcohol:water:base mixture by volume, for example about 20%, 21%, 22%, 23%, 24%, 25%, 26%, 27%, 28%, 29%, or 30% of the mixture.

In a particular embodiment, the water in the ether:alcohol:water:base mixture comprises at least 10%, at least 15%, at least 20%, at least 25%, at least 30%, at least 35%, at least 40%, at least 45%, at least 50% or at least 60% of the ether:alcohol:water:base mixture. In another embodiment, the water comprises about 10% to about 60%, about 15% to about 50%, about 20% to about 50%, about 15% to about 40%, about 15% to about 35%, about 20% to about 30% of the solvent mixture or ether:alcohol:water:base mixture by volume. In a particular embodiment, the water comprises about 20% to about 30% of the solvent mixture or ether:alcohol:water:base mixture by volume, for example about 20%, 21%, 22%, 23%, 24%, 25%, 26%, 27%, 28%, 29%, or 30% of the mixture.

In a particular embodiment, the base in the ether:alcohol:water:base mixture comprises at least 10%, at least 15%, at least 20%, at least 25%, at least 30%, at least 35%, at least 40%, at least 45%, at least 50% or at least 60% of the ether:alcohol:water:base mixture. In another embodiment, the base comprises about 10% to about 60%, about 15% to about 50%, about 20% to about 50%, about 15% to about 40%, about 15% to about 35%, about 20% to about 30% of the solvent mixture or ether:alcohol:water:base mixture by volume. In a particular embodiment, the base comprises about 20% to about 30% of the solvent mixture or ether:alcohol:water:base mixture by volume, for example about 20%, 21%, 22%, 23%, 24%, 25%, 26%, 27%, 28%, 29%, or 30% of the mixture.

In a subembodiment, the ether:alcohol:water:base mixture comprises about 20% to about 30% ether, about 20% to about 30% alcohol, about 20% to about 30% water, and about 20% to about 30% base, by volume and in any combination such the total of the ether, alcohol, water and base components is 100%.

Temperature

In one embodiment, the reaction of step (a) occurs at a temperature of less than about 100° C., less than about 95° C., less than about 90° C., less than about 85° C., less than about 80° C., less than about 75° C., or less than about 70° C. In one embodiment, the reaction of step (a) occurs at a temperature of about 25° C. to about 100° C., about 25° C. to about 95° C., about 25° C. to about 90° C., about 25° C. to about 85° C., about 25° C. to about 80° C., about 25° C. to about 75° C., about 25° C. to about 70° C., about 25° C. to about 65° C., about 35° C. to about 100° C., about 35° C. to about 95° C., about 35° C. to about 90° C., about 35° C. to about 85° C., about 35° C. to about 80° C., about 35° C. to about 75° C., about 35° C. to about 70° C., about 35° C. to about 65° C., about 45° C. to about 100° C., about 45° C. to about 95° C., about 45° C. to about 90° C., about 45° C. to about 85° C., about 45° C. to about 80° C., about 45° C. to about 75° C., about 45° C. to about 70° C., about 45° C. to about 65° C., about 50° C. to about 90° C., about 50° C. to about 85° C., about 50° C. to about 80° C., about 50° C. to about 75° C., about 50° C. to about 70° C., about 50° C. to about 65° C., about 55° C. to about 90° C., about 55° C. to about 85° C., about 55° C. to about 80° C., about 55° C. to about 75° C., about 55° C. to about 70° C., or about 55° C. to about 65° C. In a particular embodiment, the reaction occurs at about 55° C. to about 75° C., or at about 55° C., 56° C., 57° C., 58° C., 59° C., 60° C., 61° C., 61° C., 63° C., 64° C., 65° C., 66° C., 67° C., 68° C., 69° C., 70° C., 71° C., 72° C., 73° C., 74° C., or 75° C. In a particular embodiment, the reaction occurs at about 55° C. to about 70° C. In another embodiment, the reaction occurs at about 55° C. to about 65° C., or at about 60° C.

In one embodiment the reaction of step (a) occurs at the temperature of reflux of the solvent mixture. In another embodiment the reaction of step (a) occurs at a temperature below reflux of the reaction mixture or solvent system.

For the reaction of step (a), the solvent system may comprise tetrahydrofuran (THF), methanol (MeOH) and water ($H_2O$) with triethylamine ($Et_3N$) as base and be heated to 60° C. to allow a clean substitution reaction with primary and secondary amines. In one example, a large excess of the amine base is used and the solvent composition entails 1:1:1:1 triethylamine, tetrahydrofuran, methanol and water. Alternatively, an excess of the amine nucleophile can be used in the reaction of step (a) and no exogenous base is required.

In any of the foregoing processes, the reaction of the compound of Formula II

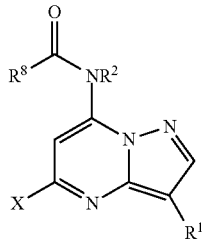

Formula II with a compound of Formula III:

$R^3R^4NH$ <span></span> Formula III is conducted at a concentration of about 0.5 moles per liter with respect to the compound of Formula III. In another embodiment, the reaction of the compound of Formula II with a compound of Formula III is conducted at a concentration of about 0.1, 0.2, 0.3, 0.4, 0.5, 0.6, 0.7, 0.8, 0.9 or 1.0 moles per liter with respect to the compound of Formula III. In another embodiment, the reaction of the compound of Formula II with a compound of Formula III is conducted at a concentration of about 0.1 to 1.0 moles per liter, about 0.2 to 0.8 moles per liter, about 0.3 to 0.6 moles per liter, or about 0.4 to 10.6 moles per liter respect to the compound of Formula III.

The reaction of step (a), or the substitution step (a), takes between 2 and 24 hours to proceed to competition depending on amine and number of equivalents used. In one embodiment, the substitution step (a) proceeds to completion in less than 24 hours, less than 20 hours, less than 18 hours, less than 16 hours, less than 14 hours, less than 12 hours, less than 10 hours, less than 8 hours, less than 6 hours, less than 4 hours, or less than 3 hours. In a particular embodiment, the substitution step (a) proceeds to completion in less than 16 hours, or less than 14 hours.

One example of the amination reaction of step (a) to produce a compound of Formula IV is the reaction of mono-Boc-1,6-hexyldiamine with a 5-chloro-pyrazolo[1,5-α]pyrimidine compound (Scheme 6).

Scheme 6

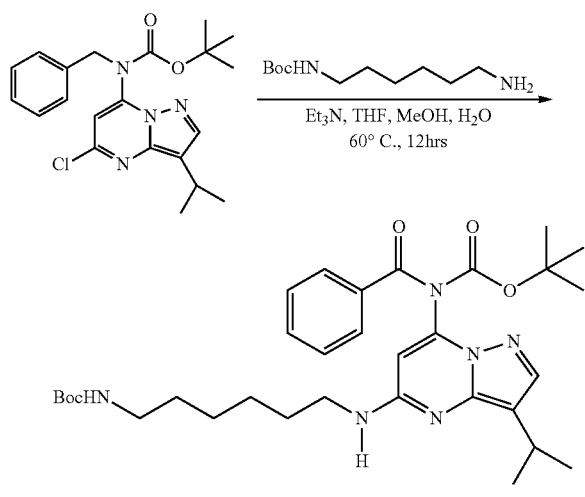

This reaction produces the compound of Formula IV in 80% yield. The products can be isolated by the addition of water and extraction with an organic solvent, for example ethyl acetate. The excess amine can be removed either by distillation or through a wash of the organic phase with aqueous citric acid solution.

In one embodiment, $R^1$ is $C_{1-5}$ alkyl, for example methyl, ethyl, propyl, iso-propyl, cyclopropyl, cyclopropylmethyl, n-butyl, sec-butyl, iso-butyl, or cyclobutyl. In a particular embodiment, $R^1$ is isopropyl.

In another embodiment, $R^1$ is halo-substituted $C_{1-5}$ alkyl, for example fluoromethyl, difluoromethyl, trifluoromethyl, fluoroethyl, difluoroethyl, trifluoroethyl including 2,2,2-trifluoroethyl; fluoropropyl, difluoropropyl, trifluoropropyl including 3,3,3-trifluoropropyl; (2,2-difluoro-cyclopropyl)methyl; chloromethyl, dichloromethyl, trichloromethyl, dichloromethyl-2,2,2-trichloroethyl; 3,3,3-trichloropropyl; (2,2-dichloro-cyclopropyl)methyl; 2,2-dibromomethyl; 3,3-dibromopropyl; or (2,2-dibromo-cyclopropyl)methyl. In a particular subembodiment, $R^1$ is fluoro-substituted $C_{1-5}$ alkyl or fluorinated $C_{1-5}$ alkyl, for example 2, 2,2-trifluoromethyl, 3,3,3-trifluoropropyl, (2,2-difluoro-cyclopropyl)methyl. In one embodiment, $R^1$ is selected from the group consisting of such as trifluoromethyl, 2,2,2-trifluoroethyl, 3,3,3-trifluoropropyl, (2,2-difluoro-cyclopropyl)methyl, When $R^1$ is a halo-substituted $C_{1-5}$ alkyl, the alkyl group can be fully or partially halogenated, for example partially fluorinated.

In one embodiment, $R^2$ is substituted or unsubstituted $C_{5-7}$ alkyl, for example pentyl, hexyl, heptyl, aminopentyl, aminohexyl, or aminoheptyl.

In one embodiment, $R^2$ is substituted or unsubstituted $C_{7-10}$ aralkyl. In one embodiment, $R^2$ is an unsubstituted aralkyl, for example benzyl. In one embodiment, the aralkyl group is —$(CH_2)_n$-aryl wherein n=1, 2, 3, 4 or 5; and aryl is phenyl, a phenyl with one to five substituents independently selected from the group consisting of halo, hydroxy, haloalkyl and alkoxy. In a particular subembodiment, n=1, 2 or 3. In another particular subembodiment, the aryl moiety of $R^2$, for example phenyl, is substituted with one substituent, for example fluoro. In another particular subembodiment, the aryl moiety of $R^2$, for example phenyl, is substituted with two, three, four or five substituents, for example fluoro. In one embodiment, the substituents on the aralkyl group independently selected from the group consisting of F, OH, $C_1$, $CF_3$, and $OR^5$, wherein $R^5$ is $C_{1-4}$ alkyl, for example methyl, ethyl, propyl, butyl. In a subembodiment, one or two substituents on the phenyl moiety are in the ortho position. In a subembodiment, one or two substituents on the phenyl moiety are in the meta position. In another subembodiment, one substitutent is in the para position.

In one embodiment, $R^2$ is substituted or unsubstituted heteroaralkyl. In one embodiment, $R^2$ is an unsubstituted heteroaralkyl. In one embodiment, the aralkyl group is —$(CH_2)_n$-heteroaryl wherein n=1, 2, 3, 4 or 5; and heteroaryl is pyramidyl, thiazoyl, or oxazolyl. Each heteroaryl can bu unsubstituted or substituted with one to five substituents independently selected from the group consisting of halo, hydroxy, haloalkyl and alkoxy. In a particular subembodiment, n=1, 2 or 3. In another particular subembodiment, the heteroaryl moiety of $R^2$ is substituted with one substituent, for example fluoro. In another particular subembodiment, the heteroaryl moiety of $R^2$ is substituted with two, three, four or five substituents, for example fluoro. In one embodiment, the substituents on the heteroaralkyl group independently selected from the group consisting of F, OH, $C_1$, $CF_3$, and $OR^5$, wherein $R^5$ is $C_{1-4}$ alkyl, for example methyl, ethyl, propyl, butyl.

In one embodiment, $R^3$ is H. In another embodiment, $R^3$ is $C_{1-4}$ alkyl, for example methyl, ethyl, propyl, or butyl. In a particular embodiment, $R^3$ is methyl. In a particular embodiment, $R^3$ is substituted by 1-4 methyl.

In one embodiment, $R^4$ is $C_{1-6}$ alkyl substituted by 1-4 substituents independently selected from OH, $NH_2$, $NR_6R_7$. In another embodiment, $R^4$ is $C_{1-6}$ alkyl substituted by 1-3 substituents independently selected from OH, $NH_2$, $NR_6R_7$. In another embodiment, $R^4$ is $C_{1-5}$ alkyl substituted by 1-3 substituents independently selected from OH, $NH_2$, $NR_6R_7$. In a particular embodiment, $R^4$ is $C_{1-4}$ alkyl substituted by 1-3 substituents independently selected from OH, $NH_2$, $NR_6R_7$; for example $R^4$ is a $C_4$ alkyl substituted with 3 OH groups. In one embodiment, $R^4$ is $C_{1-6}$ alkyl substituted by 1 $NH_2$ substituent. In one embodiment, $R^4$ is $C_{1-6}$ alkyl substituted by 1 OH group. In another embodiment, $R^4$ is $C_{1-6}$ alkyl substituted by 1-3 substituents independently selected from OH and $NH_2$.

In one embodiment, $R^8C(O)$ is a protecting group. In one embodiment, $R^8$ is $C_{1-8}$ alkyl, $C_{6-14}$ aryl, or $C_{7-20}$ arylalkyl. In another embodiment, $R^8$ is $C_{4-7}$ heterocyclic, $C_{5-15}$ heterocyclicalkyl, $C_{4-7}$ heteroaryl, or $C_{5-15}$ heteroaralkyl. In another embodiment, $R^8$ is $C_{1-8}$ alkoxy, $C_{6-14}$ aryloxy, or $C_{7-20}$ arylalkoxy. In another embodiment, $R^8$ is $C_{4-7}$ heterocyclicoxy, $C_{5-15}$ heterocyclicalkoxy, $C_{4-7}$ heteroaryloxy, or $C_{5-15}$ heteroaralkyloxy. In one embodiment, $R^8$ is substituted. In another embodiment, $R^8$ is unsubstituted.

In a particular embodiment, $R^8$ is $C_{1-8}$ alkoxy or $C_{7-20}$ arylalkoxy, for example tert-butoxy, $OC(CH_3)_2(C_6H_5)$, $OC(CH_3)(C_6H_5)_2$, or 4-methoxybenzyl-O. In one embodiment, $R^8$ is tert-butoxy, $OC(CH_3)_2(C_6H_5)$, $OC(CH_3)(C_6H_5)_2$, 4-methoxybenzyl-0, or benzylhydryloxy. In another embodiment, $R^8$ is tert-butoxy.

In another embodiment, $R^8$ is $C_{1-8}$ alkyl or $C_{6-14}$ aryl, for example methyl or phenyl. In another embodiment, $R^8$ is $C_{1-8}$ alkyl substituted by 1 to 5 halogens, for example trifluoromethyl. In another embodiment, $R^8$ is $C_{6-14}$ aryl substituted by 1 to 5 halogens, for example fluorophenyl. In another embodiment, $R^8$ is $C_{7-20}$ arylalkyl substituted by 1 to 5 halogens, for example fluorobenzyl. In another embodiment, $R^8$ is methyl, trifluoromethyl or phenyl. In one embodiment, $R^8C(O)$ is acetyl, trifluoroacetyl, or benzoyl.

In another embodiment, $R^8$ is not $C_{4-7}$ heterocyclic, $C_{5-15}$ heterocyclicalkyl, $C_{4-7}$ heteroaryl, or $C_{5-15}$ heteroaralkyl. In another embodiment, $R^8$ is not $C_{4-7}$ heterocyclicoxy, $C_{5-15}$ heterocyclicalkoxy, $C_{4-7}$ heteroaryloxy, or $C_{5-15}$ heteroaralkyloxy.

In one embodiment, $R^8C(O)$ is an equivalent protecting group of any of the foregoing embodiments, which may be removed under conditions that do not cause reactions except for deprotection.

In one embodiment, $R^8C(O)N(R^2)$— group is a carbamate or amide. In a separate embodiment, $R^8C(O)N(R^2)$— group is not a carbamate or amide.

In another embodiment, $R^8C(O)$ is a protecting group, and equivalent $_{portecting}$ rgoups may be used in place of $R^8C(O)$. For example, any equivalent protecting group, which may be removed under conditions that do not cause reactions except for deprotection. The protecting group can be used in intermediates for the preparation of compounds of Formula I, for example, a compound of Formula IIa

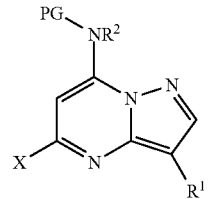

Formula IIa wherein PG is a protecting group, may be used.

In one embodiment, X is Cl. In one embodiment, X is Br. In one embodiment, X is I.

In one embodiment, X is F.

In one embodiment, the $NH_2$ and OH groups of $R^3$ and $R^4$ are protected with any suitable protecting group, such as one cleaved under acidic consitions. For example, the protected form of $NH_2$ groups is $NHC(O)R^8$ wherein $R^8$ is as defined above.

Protection of the amine and hydroxyl groups of the compounds described herein can be achieved by any means known in the art. In one aspect of the invention, the amine at the 7 position of the pyrazolo[1,5-α]pyrimidine compounds described herein can be protected with a carbonyl protecting group to produce a carbamate or amide moiety (Scheme 7).

Scheme 7

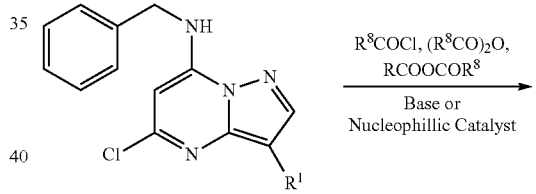

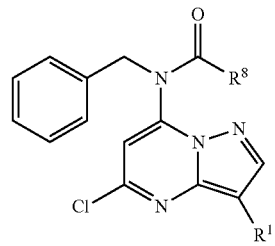

Treatment of the 7-amino pyrazolo[1,5-α]pyrimidine compounds with a carbonyl donor such as acid chlorides, acid anhydrides, mixed acid anhydrides, chloroformates and dicarbonates in the presence of either catalytic or stoichiometric base or nucleophilic catalyst such as DMAP in a suitable solvent affords the protected amine. For example, amine X can be protected as it's tert-butoxy carbamate by treatment with tert-butyl dicarbonate with catalytic N,N-dimethylamino pyridine in tetrahydrofuran at ambient temperature (Scheme 8).

Scheme 8
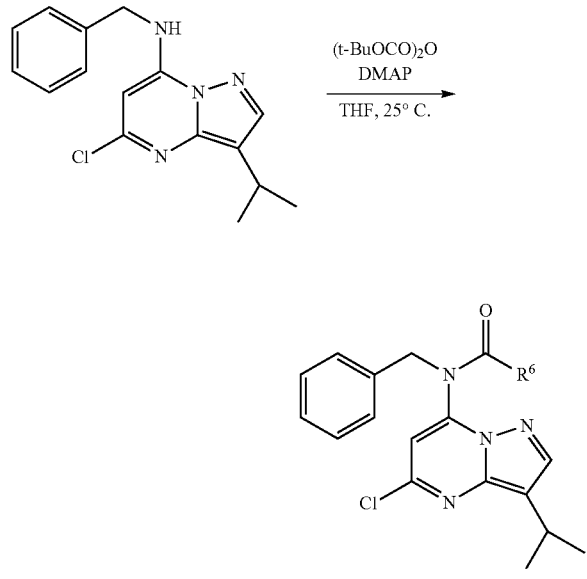
In one aspect of the invention, the compound of Formula IV is a compound selected from the group consisting of:
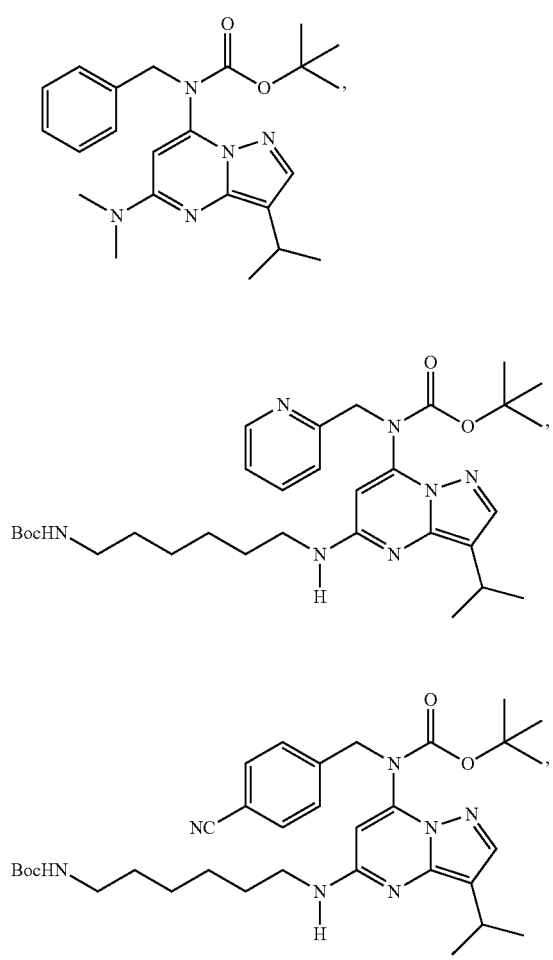
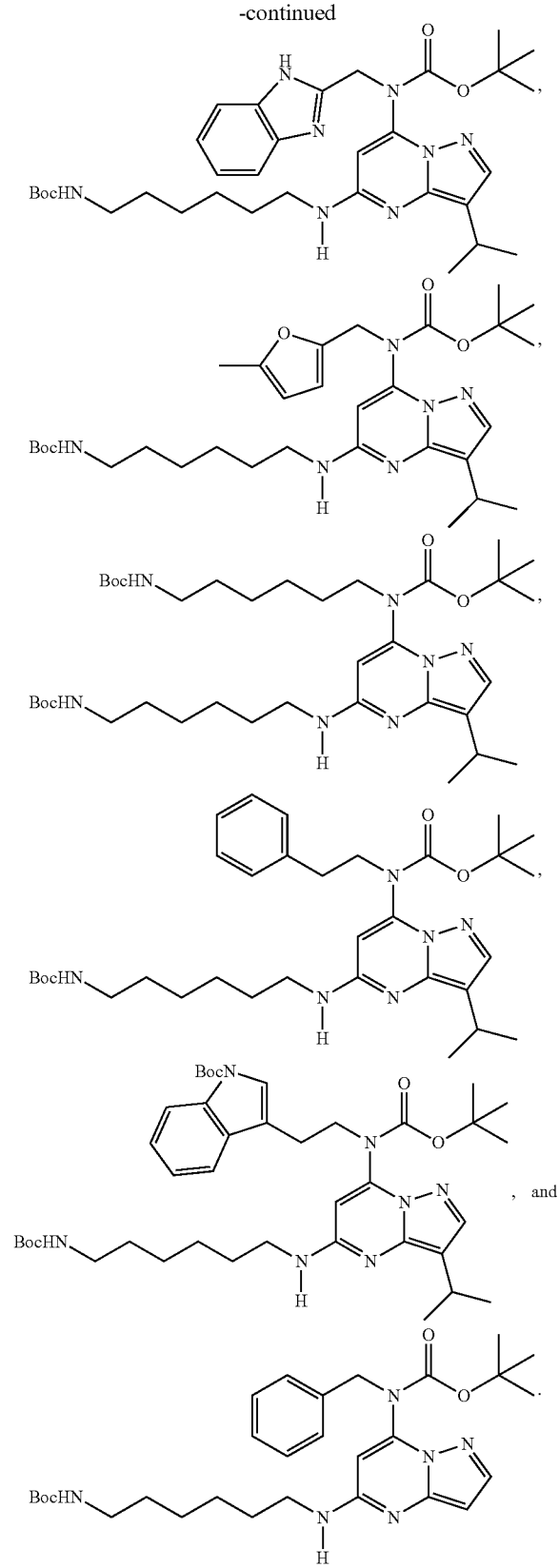
In one embodiment, the deprotection step (b) comprises the reaction of a compound of Formula IV with an acid, for example HCl, in a solvent or mixture of solvents. In one subembodiment, the solvent is anhydrous. In one embodiment the deprotection step (b) comprises an aqueous solvent, for example a mixture of an ether and water such as aqueous dioxane. In one embodiment, the solvent comprises an alcohol, an alkyl acetate, or a mixture thereof, for example methanol, methyl acetate or methanol/methyl acetate. In one embodiment, the solvent is dioxane. In another embodiment, the solvent is aqueous dioxane. In one embodiment, the deprotection step (b) removes the protecting groups from the $R^2$, $R^3$, and $R^4$ groups of the compound of Formula IV to produce a compound of Formula V or a salt thereof. In one embodiment, the protecting group, $R^8C(O)$— is replaced with a H by the deprotection step (b), for example the deprotection step (b) replaces the tert-butoxy-C(O) group with a hydrogen. An exemplary deprotection step is shown in Schemes 9a and 9b.

Scheme 9a

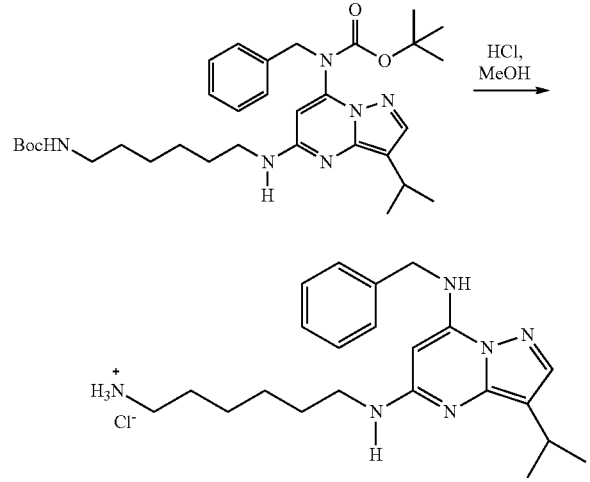

In one example of the process, the deprotection step can be achieved by treatment of a compound of Formula IV with dry HCl in methanol and methyl acetate to afford the compound of Formula V or the hydrochloride salt thereof. The hydrochloride salt may be produced when the compound of Formula V contains a basic nitrogen. For example, the hexyl diamino compound shown in Scheme 10 can undergo a deprotection to provide the final compound as a hydrochloride salt.

Scheme 10

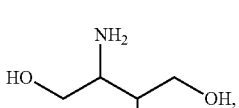

Synthesis of Amino Triol Compounds

In another aspect of the invention, a process for preparing 3-aminobutane-1,2,4-triol of Formula A is provided:

or a diastereomer thereof, which can be used in the processes described herein as a compound of Formula III, or $R^3R^4NH$ wherein $R^3$ is $CH_2OH$ and $R^4$ is $CH(OH)CH_2OH$, is provided comprising:

(i) reaction of a compound of the formula X:

$$R^bOC(O)CH(OH)CH(OH)C(O)OR^b \qquad \text{Formula X}$$

wherein $R^a$ and $R^b$ are each independently $C_{1-5}$ alkyl;

with $SOCl_2$ and a base to form a compound of Formula XI:

Formula XI

or a diastereomer thereof, (ii) addition of sodium azide to the compound of Formula XI to form an azido compound of Formula XII:

Formula XII

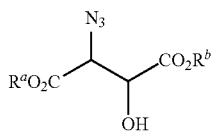

or a diastereomer thereof;
(iii) reduction of the ester groups of the compound of Formula XII with a reducing agent to form

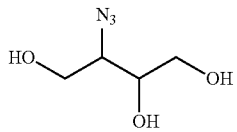

or a diastereomer thereof; and
(iv) reduction of the azido group to produce 3-aminobutane-1,2,4-triol or a diastereomer thereof.

In a particular embodiment, $R^a$ and $R^b$ are each ethyl.

In another embodiment, the base is an amine selected from the group consisting of a tertiary amine or trialkylamine, such as trimethylamine, triethylamine or diisopropylethylamine. The base can also be dimethylethanolamine, pyridine, 4-methylmorpholine, 1,8-diazabicyclo[5,4,0]-7-undecene (DBU) and the like. In one embodiment, the base is triethylamine ($Et_3N$). In another embodiment, the base is diisopropylethylamine.

In one embodiment, the reaction of step (i) is comprises a organic solvent. The organic solvent may be any solvent in which the reagents are readily dissolved. The organic solvent may be a haloalkyl, for example dichloromethane, chloroform. In a particular embodiment, the organic solvent is dichloromethane.

In one embodiment, the reaction of step (i) is conducted at a temperature lower than 25° C., for example about −10° C., about −5° C., about 0° C., about 5° C., about 10° C., or about 15° C. In a particular embodiment, the reaction of step (i) is carried out a temperature of about −5° C. to about 5° C.

In one embodiment, the reaction of step (ii) is comprises a organic solvent. The organic solvent may be any solvent in which the reagents are readily dissolved. The organic solvent may be a haloalkyl, for example dichloromethane or chloroform, or an amide, for example dimethylformamide (DMF). In a particular embodiment, the organic solvent is dimethylformamide.

In another embodiment, the reaction of step (ii) is conducted at a temperature of about 25° C. to about 70° C., for example about 25° C., about 30° C., about 35° C., about 40° C., about 45° C., about 50° C., about 55° C., about 60° C., about 65° C., or about 70° C. In a particular embodiment, the reaction of step (ii) is carried out a temperature of about 45° C. to about 55° C.

In one embodiment, the reducing agent any reducing agent which accomplishes the reduction of the esters of the compound of Formula XII, for example a hydride source, such as lithium borohydride, sodium borohydride, lithium aluminum hydride, sodium hydride, or potassium hydride. In a particular embodiment, the reducing agent is lithium borohydride.

In one embodiment, the reaction of step (iii) is comprises an alcoholic solvent. The alcoholic solvent in which the reduction readily occurs. The alcoholic solvent may be any suitable hydroxyalkane, for example methanol, ethanol, isopropanol, butanol, or tert-butanol. In a particular embodiment, the alcoholic solvent is ethanol.

In one embodiment, the reaction of step (iii) is initially conducted at a temperature lower than 25° C., for example about −10° C., about −5° C., about 0° C., about 5° C., about 10° C., or about 15° C. In a particular embodiment, the reaction of step (i) is initially conducted at a temperature of about −5° C. to about 5° C. In one embodiment, the reaction of step (iii) is initially conducted at a temperature lower than 25° C., and is allowed to warm to ambient temperature.

In one embodiment, the reaction of step (iv) is conducted on the reaction mixture of step (iii) at ambient temperature with a suitable reducing agent. The reducing agent of step (iv) can be any reducing agent, or reducing conditions, capable of reducing the azide moiety to an amine moiety. In one embodiment, the reducing conditions comprise about 1 atm of hydrogen gas and a transition metal catalyst, such as palladium metal supported on carbon (Pd/C).

An example of the process for preparing the 3-aminobutane-1,2,4-triol is shown in Scheme 11.

Scheme 11

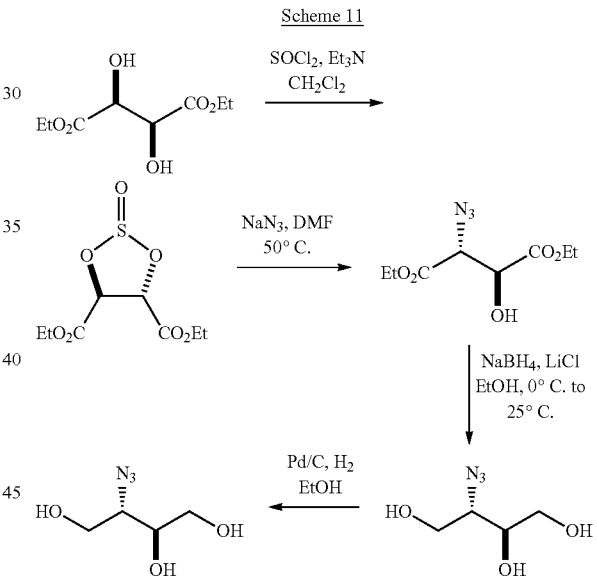

In a separate process, the process for preparing the 3-aminobutane-1,2,4-triol can be modified after step (iii) to produce a protected form of 3-aminobutane-1,2,4-triol which is suitable for use as a protected compound of Formula III. The process further comprises the protection step (iiia), wherein the product of step (iii),

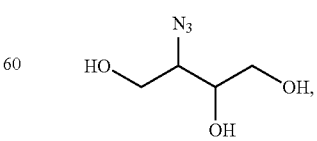

is reacted with 2,2-dimethoxypropane and a catalytic amount of p-toluenesulfonic acid monohydrate, and subsequently reduced in a reaction analogous to step (iv) to form

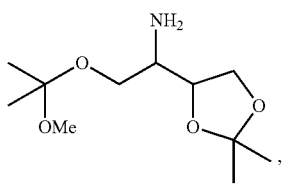 [SMILES: COC(C)(C)OCC(N)C1COC(C)(C)O1]

or a diasteromer thereof.

An example of the process for preparing a protected form of 3-aminobutane-1,2,4-triol is shown in Scheme 12.

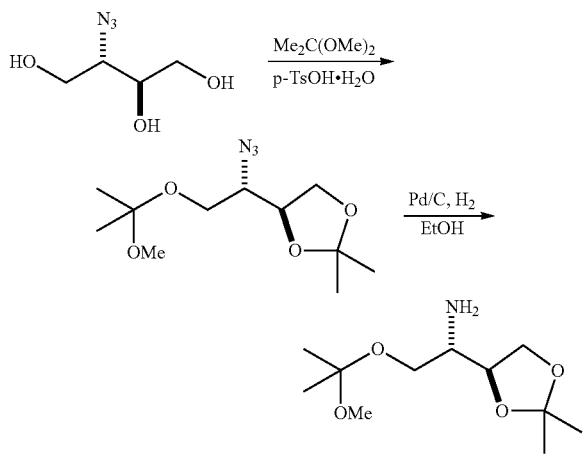

The processes for preparing 3-aminobutane-1,2,4-triol and the protected forms thereof are particularly suitable for preparing selected diastereomers of 3-aminobutane-1,2,4-triol. The specific diastereomers for which the process described herein may be used to prepare include:

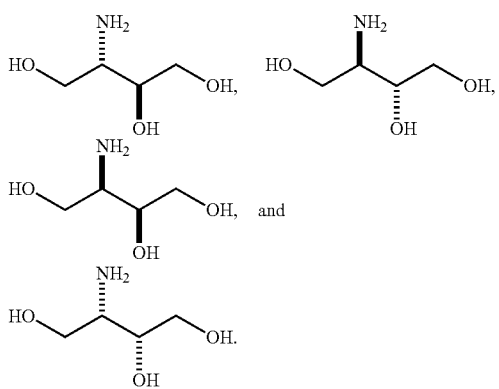

In one embodiment, the process of preparing a compound of Formula V comprises

Definitions

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "alkyl" is used herein, unless otherwise specified, refers to a saturated straight, branched, or cyclic (also identified as cycloalkyl), primary, secondary, or tertiary hydrocarbon, including but not limited to those of $C_1$ to $C_8$. Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thio, sulfonyl, ester, carboxylic acid, amide, phosphonyl, phosphinyl, thioether, oxime, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991. In certain embodiments, alkyl may be optionally substituted by one or more halo, hydroxy, heterocyclic, heteroaryl, carboxy, —$NR^xR^y$, alkoxycarbonyl, —$NR^yC(O)R^x$, —$NR^yC(O)NR^xR^y$, —$NR^yC(O)OR^x$, —$OC(O)NR^xR^y$, —$OR^x$, —$C(O)R^x$, —$S(O)_n$—$R^x$, —$C(O)$—$NR^xR^y$, and/or cyano. In certain embodiments, the alkyl may be optionally substituted by one or more halo, alkyl, lower alkyl, alkenyl, cycloalkyl, acyl, hydroxy, hydroxyalkyl, heterocyclic, heteroaryl, aryl, amino, aminoalkyl, —$NR^xR^y$, oxo, cyano, carboxy, carboxyalkyl, alkoxycarbonyl, —$OR^x$, —$C(O)R^x$, —$C(O)$—$NH_2$, —$C(O)$—$N(H)R^x$, —$C(O)$—$N(H)OR^x$, —$C(O)$—$NR^xR^y$, —$NR^yC(O)R^x$, —$NR^yC(O)NR^xR^y$, —OC(O)$NR^xR^y$, —$NRYC(O)OR^x$, —$S(O)_n$—$R^x$, —$S(O)_2$—$NH_2$, —$S(O)_n$—$N(H)R^x$ and/or —$S(O)_2$—$NR^xR^y$, wherein $R^x$ and $R^y$ are each independently $C_{1-6}$ alkyl.

The term "lower alkyl," unless otherwise specified, refers to a $C_1$ to $C_5$ saturated or unsaturated straight, branched carbon chain such as methyl, ethyl, isopropyl, n-butyl, tert-butyl, n-pentyl, sec-pentyl, 3-methylpentyl, and the like, or if appropriate, a cyclic (for example, cyclopropyl) alkyl group.

The term "halo" or "halogen," refers to chloro, bromo, iodo, or fluoro.

The term "heteroaryl" or "heteroaromatic," refers to an aromatic that includes at least one sulfur, oxygen, nitrogen or phosphorus in the aromatic ring. The term "heterocyclic" refers to a non-aromatic cyclic group wherein there is at least one heteroatom, such as oxygen, sulfur, nitrogen, or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, pteridinyl, aziridines, thiazole, isothiazole, oxadiazole, thiazine, pyridine, pyrazine, piperazine, piperidine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic or heterocyclic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. Nonlimiting examples include dihydropyridine and tetrahydrobenzimidazole. In some embodiment, the heteroaryl may be optionally substituted by one or more halo, alkyl, lower alkyl, alkenyl, cycloalkyl, acyl, hydroxy, hydroxyalkyl, heterocyclic, heteroaryl, aryl, amino, aminoalkyl, —$NR^xR^y$, oxo, cyano, carboxy, carboxyalkyl, alkoxycarbonyl, —$OR^x$, —$C(O)R^x$, —$C(O)$—$NH_2$, —$C(O)$—$N(H)R^x$, —$C(O)$—$N(H)OR^x$, —$C(O)$—$NR^xR^y$, —$NR^yC(O)R^x$, —$NR^yC(O)NR^xR^y$, —$OC(O)NR^xR^y$, —$NR^yC(O)OR^x$, —$S(O)_n$—$R^x$, —$S(O)_2$—$NH_2$, —$S(O)_n$—$N(H)R^x$ and/or —$S(O)_2$—$NR^xR^y$, wherein $R^x$ and $R^y$ are each independently $C_{1-6}$ alkyl.

Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term "aryl," unless otherwise specified, refers to a carbon based aromatic ring, including phenyl, biphenyl, or naphthyl. The aryl group can be optionally substituted with one or more moieties selected from the group consisting of hydroxyl, acyl, amino, halo, alkylamino, alkoxy, aryloxy, nitro, cyano, sulfonic acid, sulfate, phosphonic acid, phosphate, or phosphonate, either unprotected, or protected as necessary as known to those skilled in the art, for example, as taught in Greene, et al., *Protective Groups in Organic Synthesis*, John Wiley and Sons, Second Edition, 1991. In certain embodiments, the aryl group is optionally substituted by one or more halo, alkyl, lower alkyl, alkenyl, cycloalkyl, acyl, hydroxy, hydroxyalkyl, heterocyclic, heteroaryl, aryl, amino, aminoalkyl, —$NR^7R^8$, oxo, cyano, carboxy, carboxyalkyl, alkoxycarbonyl, —$OR^9$, —$C(O)R^9$, —$C(O)$—$NH_2$, —$C(O)$—$N(H)R^7$, —$C(O)$—$NR^7R^8$, —$NR^7C(O)R^9$, —$NR^7C(O)OR^9$, —$S(O)_n$—$R^9$, —$S(O)_2$—$NH_2$, —$S(O)_2$—$N(H)R^7$ and/or —$S(O)_2$—$NR^7R^8$.

The term "aralkyl" or "arylalkyl" unless otherwise specified, refers to an aryl group as defined above linked to the molecule through an alkyl group as defined above. The term "alkaryl," unless otherwise specified, refers to an alkyl group as defined above linked to the molecule through an aryl group as defined above. Other groups, such as alkoxyalkyl, alkoxycarbonylalkyl, alkylaminoalkyl, alkylthioalkyl, amidoalkyl, aminoalkyl, carboxyalkyl, dialkylaminoalkyl, haloalkyl, heteroaralkyl, heterocyclicalkyl, hydroxyalkyl, sulfonamidoalkyl, sulfonylalkyl and thioalkyl are named in a similar manner.

The term "alkoxy" or "alkyloxy" unless otherwise specified, refers to a moiety of the structure —O-alkyl, wherein alkyl is as defined above.

The term "aryloxy," unless otherwise specified, refers to a moiety of the structure -D-aryl, wherein aryl is as defined above.

The term "heteroaryloxy," unless otherwise specified, refers to a moiety of the structure —O-heteroaryl, wherein heteroaryl is as defined herein.

The term "aralkoxy" or "arylalkoxy" unless otherwise specified, refers to an aryl group as defined above linked to the molecule through an alkoxy group as defined above. The term "alkoxyaryl," unless otherwise specified, refers to an alkoxy group as defined above linked to the molecule through an aryl group as defined above. Other groups, such as heteroaryloxy, heteroarylalkyloxy, heterocyclicalkoxy, or heterocyclicalkyloxy are named in a similar manner.

The term "acyl," refers to a group of the formula —C(O)R' wherein R' is an alkyl, aryl, alkaryl or aralkyl group, or substituted alkyl, aryl, aralkyl or alkaryl.

The term "alkenyl" The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to (C2-C8)alkenyl groups, such as vinyl, allyl, butenyl, pentenyl, hexenyl, butadienyl, pentadienyl, hexadienyl, 2-ethylhexenyl,2-propyl-2-butenyl,4-(2-methyl-3-butene)-pentenyl. An alkenyl group can be unsubstituted or substituted with one or two suitable substituents.

The term "carbonyl" refers to a functional group composed of a carbon atom double-bonded to an oxygen atom: —C=O.

The term "amino" indicates presence of —$NH_2$.

The term "thio" indicates the presence of a sulfur group. The prefix thio-denotes that there is at least one extra sulfur atom added to the chemical. The prefix 'thio-' can also be placed before the name of a compound to mean that an oxygen atom in the compound has been replaced by a sulfur atom. Although typically the term "thiol" is used to indicate the presence of —SH, in instances in which the sulfur atom would be have improper valance a radical if the hydrogen is improperly designated, the terms 'thio-' and 'thiol' are used interchangeably, unless otherwise indicated.

The term "amido" indicates a group —NH—C(O)—R.

The term "carboxy" designates the terminal group —C(O)OH.

The term "sulfonyl" indicates a group —S(=O)$_2$—R'.

The term "pharmaceutically acceptable salt" refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —$NR^+$ $A^-$, wherein R is as defined above and A is a counterion, including chloride, bromide, iodide, —O-alkyl, toluene-sulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term "protected" as used herein and unless otherwise defined refers to a group that is added to an oxygen, nitrogen, or phosphorus atom to prevent its further reaction or for other purposes, or a group described elsewhere herein as a protecting group. A wide variety of oxygen and nitrogen protecting groups are known to those skilled in the art of organic synthesis.

The term "carbocyclic ring" or "cycloalkyl" or "cyclic alkyl" refers to a cyclic group of carbon and hydrogen atoms. The term includes both aromatic and non-aromatic rings. Non-limiting examples of carbocyclic rings includes cyclopropyl, cyclobutyl and phenyl. As used herein, a "heterocyclic ring" refers to a cyclic group of carbon and hydrogen atoms which contains at least one other non-carbon atom as a part of the ring. A heterocyclic ring may possess aromatic character (i.e., heteroaryl) or non-aromatic character. Carbocyclic and heterocyclic rings according to the invention may be substituted unless stated otherwise, and typically with halogen, alkyl or alkoxy groups. The term "non-aromatic character" includes unsaturated ring systems without aromatic character, as well as partially or fully saturated carbocyclic or heterocyclic ring systems. The term "unsaturated" or "partially saturated" refers to groups of atoms that share more than one valence bond, such that the overall structure contains at least one multiple bond (e.g. a C=C or C=N bond). Examples of "partially saturated" chemical groups includes alkenyl, alkynyl, cycloalkenyl and cycloalkynyl groups (e.g., vinyl or cyclohexenyl.) The term "fully saturated" refers to a group of atoms connected with single bonds and include alkyls and cycloalkyls, (e.g., methyl or cyclohexyl). As used herein "alkenyl" is a generic term that refers to a carbon chain containing at least one double bond and preferably containing 2-6 carbon atoms. The carbon chain might be straight or branched and, if it is not stated otherwise in the context, may be substituted with halogen or other substituents such as hydroxyl, alkoxyl, amino or substituted amino Non-aromatic carbocyclic rings include substituted or unsubstituted cycloalkyl, or cycloalkenyl systems, wherein cycloalkyl refers to a fully saturated ring, and cycloalkenyl refers to a ring containing at least one double bond. Most typically, these are monocyclic groups containing up to 6 ring members. The carbocyclic rings can be substituted with at least one "substituent" as defined herein.

Heteroaryl groups contemplated by the invention include monocyclic or bicyclic structures containing usually up to 12 ring members with heteroatoms selected from S, N or O. The bicyclic moieties are formed from fused rings (usually 5-6 membered rings) and typically contain up to four heteroaroms. Non-limiting examples of five-membered monocyclic heteroaryl groups include imidazole, pyrrole, furan, thiophene, oxazole, and pyrazole. Non-limiting examples of six-membered monocyclic heteroaryl groups include pyridine, pyrimidine, and pyrazine. Furthermore, non-limiting examples of bicyclic heteroaryls include indole, quinoline, and benzothiazole.

The term "substituent" refers to any chemical moiety that can take the place of hydrogen or hydrogens in satisfying the valence of a carbon atom. Non-limiting examples of substituents contemplated by the invention include straight or branched alkyl, straight or branched alkenyl, straight or branched alkynyl, hydroxy, alkoxy, halogen, alkylmercapto, nitro, cyano, carbocyclic, heterocyclic, benzyl, trifluoromethyl. Moreover, a "substituent" according to the invention may include —COOH, —COOR$^x$, —COR$^x$, —SO$_2$R$^x$, —CONH$_2$, CONHR$^x$, —CONHR$^x$R$^y$, —NH$_2$, —NHR$^x$, —NHR$^x$R$^y$, —CH=NNH$_2$, —OCONH$_2$, —OCONHR$^x$, OCONHR$^x$R$^y$, wherein R$^x$ and R$^y$ are independently alkyl groups.

When there are two substituents, one on each of two vicinal carbon atoms in a carbocyclic or heterocyclic ring, the two substituents themselves may be linked to form a heteroaryl ring, non-aromatic carbocyclic ring or non-aromatic heterocyclic ring. Alternatively, in some embodiments where two substituents are in the 1,3-positions with respect to each other, the substituents may also be linked to form a carbocyclic or non-aromatic heterocyclic ring. The heteroatoms within such rings are usually selected from O, N and S. Rings formed in this manner have typically up to 6 members and up to 3 heteroatoms. A few representative examples of such rings are shown below:

The invention includes all the compounds or products of the processes described herein as well as their salts. The term "salt" refers to an ionic form of these compounds obtained by addition of base (e.g. sodium hydroxide, magnesium hydroxide) or acid. If acid is used, the acid may be an organic acid (e.g. citric acid or acetic acid) or an inorganic acid (e.g. hydrochloric acid or sulphuric acid).

Stereochemistry

Since some of the compounds have chiral centers, it is possible to have several diastereoisomers bearing R or S stereochemistry at each center. This invention covers all possible diastereoisomers and their mixtures. It should be understood that the various possible stereoisomers of the groups mentioned above and herein are within the meaning of the individual terms and examples, unless otherwise specified. As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

The term "stereoisomers" refers to isomeric molecules whose atomic connectivity is the same but whose atomic arrangement in space is different.

The term "enantiomers" refers to compounds that are stereoisomers that are nonsuperimposable complete mirror images of each other. Enantiomers have, when present in a symmetric environment, identical chemical and physical properties except for their ability to rotate plane-polarized light by equal amounts but in opposite directions.

The term "racemic" refers to a mixture of equal parts of an optically active isomer and its enantiomer.

The term "diastereomers" refers to a pair stereoisomers that are not mirror images of each other and one or more stereogenic centers differ between the two stereoisomers, or one or more chiral centers have opposite configurations between the two stereoisomers.

The diastereomeric compounds described herein can be isolated, purified or separated into individual diastereomers by any means known in the art.

Protecting Groups

Protecting groups and the methods by which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and also in Theodora W. Greene, "Protective Groups in Organic Synthesis", John Wiley & Sons, New York 1981. It is characteristic of protecting groups that they can be removed easily, i.e. without undesirable secondary reactions taking place, for example by solvolysis, reduction, photolysis or also under physiological conditions A protected amino group may, for example, be in the form of a readily cleavable acyl amino, arylmethylamino, etherified mercaptoamino, 2-acyl-lower alk-1-en-yl-amino, silylamino or stannylamino group or in the form of an azido group.

In a corresponding acylamino group, acyl is, for example, the acyl radical of an organic carboxylic acid having, for example, up to 18 carbon atoms, especially of an unsubstituted or substituted, for example halo- or aryl-substituted, alkanecarboxylic acid or an unsubstituted or substituted, for example halo-, lower alkoxy- or nitro-substituted, benzoic acid, or of a carbonic acid ester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trifluoro-acetyl, unsubstituted or substituted, for example halo-, lower alkoxy- or nitro-substituted, benzoyl, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert-lower alkoxycarbonyl, for example tert-butoxycarbonyl, aryl-methoxycarbonyl having one or two aryl radicals which are preferably phenyl that is unsubstituted or is mono- or poly-substituted, for example, by lower alkyl, especially tert-lower alkyl, such as tert-butyl, lower alkoxy, such as methoxy, hydroxy, halogen, for example chlorine, and/or by nitro, such as unsubstituted or substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, aroyl-methoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2, 2,2-trichloroethoxycarbonyl, 2-bromoethoxy-carbonyl or 2-iodoethoxycarbonyl, or 2-(trisubstituted silyl)-ethoxycarbonyl wherein each substituent independently is an aliphatic, araliphatic, cycloaliphatic or aromatic hydro¬ carbon radical having up to 15 carbon atoms that is unsubstituted or substituted, for example, by lower alkyl, lower alkoxy, aryl, halogen or by nitro, such as corresponding, unsubstituted or substituted, lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-tri-phenylsilylethoxycarbonyl.

Other acyl radicals that are suitable as amino-protecting groups are also corresponding radicals of organic phosphoric, phosphonic or phosphinic acids, such as di-lower alkyl-phosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, unsub¬ stituted or substituted, for example nitro-substituted, di-(phenyl-lower alkyl)-phosphoryl, for example dibenzylphosphoryl or di-(4-nitrobenzyl)-phosphoryl, unsubstituted or substi¬tuted phenyloxyphenyl-phosphonyl, for example phenyloxyphenylphosphonyl, di-lower alkylphosphinyl, for example diethylphosphinyl, or unsubstituted or substituted diphenylphosphinyl, for example diphenylphosphinyl.

In an arylmethylamino group that is a mono-, di- or, especially, a tri-arylmethylamino group, the aryl radicals are, especially, unsubstituted or substituted phenyl radicals. Such groups are, for example, benzyl-, diphenylmethyl- and, especially, trityl-amino.

An etherified mercapto group in an amino group protected by such a radical is especially arylthio or aryl-lower alkylthio wherein aryl is especially phenyl that is unsubstituted or substituted, for example, by lower alkyl, such as methyl or tert-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, for example 1-acetyl-prop-1-en-2-yl, or 1-lower alkoxycarbonyl-prop-1-en-2-yl, for example 1-ethoxycarbonyl-prop-1-en-2-yl.

Preferred amino-protecting groups are acyl radicals of carbonic acid esters, especially tert-butoxycarbonyl, benzyloxycarbonyl that is unsubstituted or substituted, for example as indicated, for example 4-nitro-benzyloxycarbonyl, or diphenylmethoxycarbonyl, or 2-halo-lower alkoxycarbonyl, such as 2,2,2-trichloroethoxycarbonyl, also trityl or formyl. Carboxy groups are usually protected in esterified form, such ester groupings being readily cleavable under mild conditions. Carboxy groups protected in that manner contain as esterifying groups especially lower alkyl groups that are branched in the 1-position or suitably substituted in the 1- or 2-position. Preferred carboxy groups in esterified form are inter alia tert-lower alkoxycarbonyl, for example tert-butoxycarbonyl, arylmethoxy-carbonyl having one or two aryl radicals which are phenyl radicals that are unsubstituted or mono- or poly-substituted, for example, by lower alkyl, such as tert-lower alkyl, for example tert-butyl, lower alkoxy, such as methoxy, hydroxy, halogen, for example chlorine, and/or by nitro, such as benzyloxycarbonyl that is unsubstituted or substituted, for example as mentioned above, for example 4-methoxybenzyloxycarbonyl or 4-nitro-benzyloxycarbonyl, or diphenylmethoxycarbonyl that is unsubstituted or substituted, for example as mentioned above, for example diphenylmethoxycarbonyl or di-(4-methoxy-phenyl)-methoxycarbonyl, 1-lower alkoxy-lower alkoxycarbonyl, such as methoxy-methoxycarbonyl, 1-methoxyethoxycarbonyl or 1-ethoxymethoxycarbonyl, 1-lower alkyl-thio-lower alkoxycarbonyl, such as 1-methylthiomethoxycarbonyl or 1-ethylthioethoxy-carbonyl, aroylmethoxycarbonyl wherein the aroyl group is benzoyl that is unsubstituted or substituted, for example by halogen, such as bromine, for example phenacyloxy carbonyl, 2-halo-lower alkoxycarbonyl, for example 2, 2,2-trichloroethoxycarbonyl, 2-bromoethoxycarbonyl or 2-iodoethoxycarbonyl, or 2-(trisubstituted silyl)ethoxycarbonyl wherein each substituent independently is an aliphatic, araliphatic, cycloaliphatic or aromatic hydrocarbon radical that is unsubstituted or substituted, for example, by lower alkyl, lower alkoxy, aryl, halogen and/or by nitro, such as corresponding, unsubstituted or substituted, lower alkyl, phenyl-lower alkyl, cycloalkyl or phenyl, for example 2-tri-lower alkylsilylethoxycarbonyl, 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

The organic silyl and stannyl radicals mentioned above and hereinafter contain preferably lower alkyl, especially methyl, as substituents of the silicon or tin atoms. Corresponding silyl or stannyl groups are especially tri-lower alkylsilyl, especially trimethylsilyl, or dimethyl-tert-butyl-silyl, or correspondingly substituted stannyl, for example tri-n-butyl-stannyl.

Preferred protected carboxy groups are tert-lower alkoxycarbonyl, such as tert-butoxy carbonyl, and especially benzyloxycarbonyl that is unsubstituted or substituted, for example, as mentioned above, such as 4-nitrobenzyloxycarbonyl, or diphenylmethoxy carbonyl, especially 2-(trimethylsilyl)ethoxycarbonyl.

Hydroxy-protecting groups are, for example, acyl radicals, such as unsubstituted or substituted, for example halo-substituted, lower alkanoyl, such as 2,2-dichloroacetyl, or acyl radicals of carbonic acid semiesters, especially tert-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, also trityl or formyl, or organic silyl or stannyl radicals, or readily removable etherifying groups, such as tert-lower alkyl, for example tert-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxy-ethyl, 1-ethoxy-ethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also unsubstituted or substituted 1-phenyl-lower alkyl, such as unsubstituted or substituted benzyl or diphenylmethyl, suitable substituents of the phenyl radicals being, for example, halogen, such as chlorine, lower alkoxy, such as methoxy, and/or nitro.

The removal of protecting groups that are not constituents of the desired end product of formula I, for example the carboxy-, amino-, hydroxy- or carbamoyl-protecting groups, is effected in a manner known per se, for example by means of solvolysis, especially hydrolysis, alcoholysis or acidolysis, or by means of reduction, especially hydrogenolysis or chemical reduction, as appropriate stepwise or simultaneously, it being possible also to use enzymatic methods, for example acidolysis, such as treatment with trifluoroacetic acid or formic acid, or reduction, such as treatment with zinc and acetic acid, or with hydrogen and a hydrogenation catalyst, such as a palladium-on-carbon catalyst.

When several protected functional groups are present, the protecting groups are preferably so chosen that more than one such group can be removed simultaneously.

A protected amino group is freed in a manner known per se and, according to the nature of the protecting groups, in various ways, preferably by solvolysis or reduction. 2-Halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-(tri-substituted silyl)-ethoxycarbonylamino, can be cleaved by treatment with a suitable acid, for example formic acid or trifluoroacetic acid, or with hydrochloric acid in ethyl acetate or dioxane; unsubstituted or substituted benzyloxycarbonylamino can be cleaved, for example, by means of hydrogenolysis, i.e. by treatment with hydrogen in the presence of a suitable hydrogenation catalyst, such as a palladium catalyst; unsubstituted or substituted triaryl-methylamino or formylamino can be cleaved, for example, by treatment with an acid, such as a mineral acid, for example hydrochloric acid, or an organic acid, for example formic, acetic or trifluoroacetic acid, where appropriate in the presence of water; and an amino group protected by an organic silyl group can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and subsequent solvolysis, such as alcoholysis or hydrolysis, of the resulting condensation product. An amino group protected by 2-substituted silylethoxycarbonyl can be converted into the free amino group also by treatment with a salt of hydrofluoric acid that yields fluoride anions.

Tert-lower alkoxycarbonyl, lower alkoxycarbonyl substituted in the 2-position by an organic silyl group or in the 1-position by lower alkoxy or by lower alkylthio, or unsubstituted or substituted diphenylmethoxycarbonyl can be converted into free carboxy, for example, by treatment with a suitable acid, such as formic acid or trifluoroacetic acid, where appropriate with the addition of a nucleophilic compound, such as phenol or anisole. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by chemical reduction, for example by treatment with an alkali metal dithionite, such as sodium dithionite, or with a reducing metal, for example zinc, or a reducing metal salt, such as a chromium(II) salt, for example chromium(U) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid that yields the fluoride anion, such as an alkali metal fluoride, for example sodium or potassium fluoride, in the presence of a macrocyclic polyether ("crown ether"), or with a fluoride of an organic quaternary base, such as tetra-lower alkylammonium fluoride or tri-lower alkylarylammonium fluoride, for example tetraethylammonium fluoride or tetra-butylammonium fluoride, in the presence of an aprotic, polar solvent, such as dimethylsulfoxide or N,N-dimethylacetamide.

A hydroxy group protected by a suitable acyl group, an organic silyl group or by unsubstituted or substituted 1-phenyl-lower alkyl is freed analogously to a correspondingly protected amino group. Hydroxy protected by unsubstituted or substituted 1-phenyl-lower alkyl, for example benzyl, is freed preferably by catalytic hydrogenation, for example in the presence of a palladium-on-carbon catalyst. A hydroxy group protected by 2,2-di-chloroacetyl is freed, for example, by basic hydrolysis, and a hydroxy group etherified by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Hydroxy etherified by an organic silyl radical, for example trimethylsilyl, can also be freed with a salt of hydrofluoric acid that yields fluoride anions, for example tetrabutylammonium fluoride.

The processes described herein are more fully understood by reference to the following examples, which are not intended to limit the scope of the invention.

EXAMPLES

Example 1

Synthesis of Compounds of Formula I

Compounds of Formula I can be prepared according to Scheme 13.

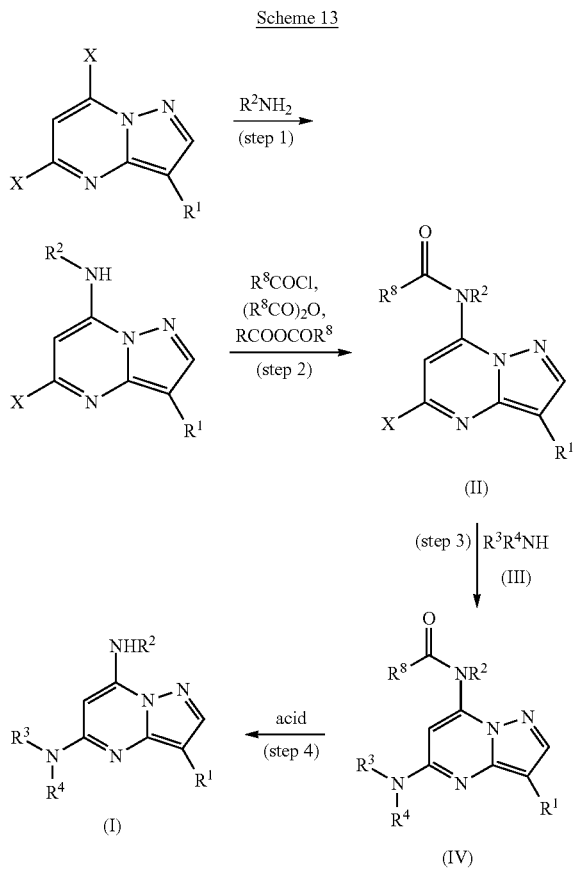

The 5,7-dihalo-pyrazolo[1,5-α]pyrimidine compound can be prepared according to literature methods, for example the methods described in International Patent Application No. PCT/US2008/65988.

Step 1. The 5,7-dihalo-pyrazolo[1,5-α]pyrimidine compound is reacted with an amine compound $R_2NH_2$ to give produce a halo-pyrazolo[1,5-α]-pyrimidin-amine compound. Two equivalents of amine nucleophile can be used or alternatively one equivalent in the presence of exogenous base. The reaction can be carried out in a protic solvent such as an alcohol, in the presence of a tertiary amine or equivalent organic base (e.g., triethylamine, di-iso-propylethylamine or N''-tert-butyl-N',N',N,N-tetramethylguanidine; see D. S. Williamson et al., *Bioorg. Med. Chem. Lett.*, 15, 863-867 (2005)).

The amine compound $R_2NH_2$ can be obtained from commercial sources or can be prepared by a large number of synthetic methods when known to those trained in the art.

Step 2. The halo-pyrazolo[1,5-α]-pyrimidin-amine compound is next protected with a protection group. The protection is not particularly limited and can be, for example, selected from carbamates (e.g. tert-butyl carbamate, benzyl carbamate) or amides (e.g. formamide, acetamide, benzamide). In a particularly preferred embodiment, the protecting group is a carbamate, most preferably tert-butylcarbamate (Boc).

The protection group is installed by reaction of the halo-pyrazolo[1,5-α]-pyrimidin-amine compound with, for example, an $R^8COCl$, $(R^8CO)_2O$, or $RCOOCOR^8$, to produce compound (II). The protection reaction to synthesize compound (II) can be carried out in several ways that are well documented in literature and known to those trained in the art. When Boc is chosen as a protective group, the reaction is typically carried out with the use of di-tert-butyl dicarbonate in a non-aqueous solvent such as acetonitrile, dimethyl sulfoxide, dichloromethane or in an aqueous solvent optionally together with a miscible or non-miscible co-solvent. The reaction can be carried out in a presence of base such as sodium hydroxide or triethylamine.

Step 3. Compound (II) is reacted with an amine compound (III) to produce a compound (IV). This amination step is conducted in an ether:alcohol:water solvent and optionally includes a base, for example triethylamine. The reaction mixture is usually heated slightly, for example to a temperature around 60° C.

Amine compound (III) can be purchased or synthesized accordingly to synthetic methods well known to those trained in the art.

Step 4. Deprotection of the nitrogen protecting group, $R^8C(O)$—, in compound (IV) is carried out under standard conditions well known to those trained in the art and which yields the desired compound (I). For example. reaction of compound IV with acid, such as HCl, in a solvent, such as methanol, produces the corresponding compound (I) or a salt thereof if the compound (I) contains a basic nitrogen.

Example 2

Synthesis of BS-194

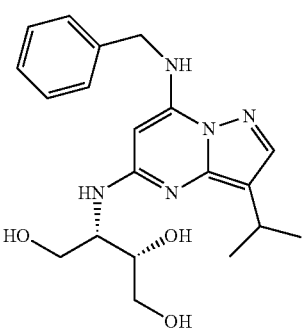

BS-194

Step 1. Synthesis of 3-Isopropyl-5,7-dihydroxypyrazolo[1,5-α]pyrimidine

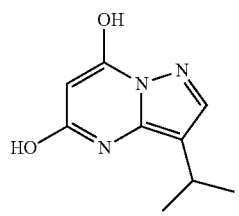

A solution of LDA (60.2 mL, 120 mmol, 2 M in THF) in THF (40 mL) was cooled to −78° C. Isovaleronitrile (10 g, 120 mmol) was added and the solution stirred for 10 min at −78° C. The reaction mixture was added to a solution of ethyl formate (10.2 mL, 126 mmol) in THF (50 mL) at −78° C. The solution was stirred for 30 min at this temperature and then allowed to warm to rt and stirred for additional 16 h. 1 M Hydrochloric acid was added until the pH was approximately pH=3. The red organic phase was separated and the aqueous phase extracted with ethyl acetate (3×75 mL). The combined organic phases were dried over MgSO$_4$ and the solvent evaporated in vacuo. The resulting residue was purified by column chromatography on silica (diethyl ether:hexanes=1:2) to yield 2-formyl-3-methylbutanenitrile as a yellow oil (9.97 g, 75%).

Next, 2-formyl-3-methylbutanenitrile (9.97 g, 90 mmol), hydrazine hydrate (5.68 mL, 117 mmol) and glacial acetic acid (9.02 mL, 158 mmol) were dissolved in EtOH (250 mL) and the mixture was heated under reflux for 16 h. The reaction was then concentrated to approximately one third of the original volume. The residue was diluted with sat. NaHCO$_3$ (100 mL) and the product extracted with CH$_2$Cl$_2$ (3×100 mL). The combined organic fractions were washed with brine, dried over MgSO$_4$ and the solvent was removed in vacuum. Crude 4-isopropyl-1H-pyrazol-5-amine was obtained as a yellow oil (7.17 g, 64%).

Sodium (1.58 g, 68.7 mmol) was dissolved in EtOH (250 mL) and to this solution was added 4-isopropyl-1H-pyrazol-5-amine (7.17 g, 57 mmol) and diethyl malonate (10.2 mL, 63 mmol). The solution was heated under reflux for 16 h, cooled to rt and concentrated in vacuo. The residue was dissolved in water (60 mL) and acidified to pH=3 with 2 M HCl and the formed precipitate collected by filtration. 3-Isopropyl-5,7-dihydroxypyrazolo[1,5-α]pyrimidine was obtained as an off-white solid (8.10 g, 35% over three steps). M.p. 242-243° C. (ethanol).

Step 2. Synthesis of 5,7-Dichloro-3-isopropylpyrazolo[1,5-α]pyrimidine

To a suspension of 3-Isopropyl-5,7-dihydroxypyrazolo[1,5-α]pyrimidine (3.95 g, 20.4 mmol) in POCl$_3$ (38.2 mL, 410 mmol) was added N,N-dimethylaniline (1.73 mL, 13.6 mmol) and the mixture was heated under reflux for 16 h. During this time the pyrimidine went into solution. The POCl$_3$ was distilled off and the concentrate poured onto ice (~50 g). The product was extracted with extracted with CH$_2$Cl$_2$ (3×50 mL) and the combined organic fractions were washed with brine and dried over Na$_2$SO$_4$. After concentration the crude product was purified by column chromatography on silica (ethyl acetate:hexanes=1:20) to yield 5,7-dichloro-3-isopropylpyrazolo[1,5-α]pyrimidine as a yellow solid (3.81 g, 81%).

M.p. 43-44° C. (ethyl acetate). $^1$H NMR (CDCl$_3$, 300 MHz) δ 8.10 (s, 1H), 6.93 (s, 1H), 3.31 (hep, J=6.8 Hz, 1H), 1.37 (d, J=6.8 Hz, 6H). $^{13}$C NMR (CDCl$_3$, 75 MHz) δ 147.3, 144.6, 143.9, 139.4, 119.4, 107.9, 23.6, 23.2. IR (neat) $v_{max}$=2963, 1641, 1496, 1098, 618. MS m/z (CI) 230 (M+H). HRMS (CI) Calc.: 230.0252; Found: 230.0248 Microanalysis Calc: C, 46.98; H, 3.94; N, 18.26; Found: C, 47.02; H, 3.87; N, 18.28.

Step 3. Synthesis of N-Benzyl-5-chloro-3-isopropylpyrazolo[1,5-α]pyrimidin-7-amine

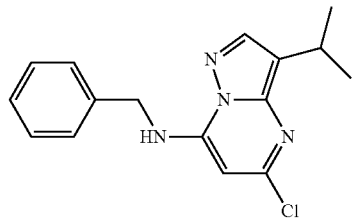 [SMILES: CC(C)c1cnn2c(NCc3ccccc3)cc(Cl)nc12]

5,7-dichloro-3-isopropylpyrazolo[1,5-α]pyrimidine (500 mg, 2.17 mmol) and benzyl amine (0.52 mL, 4.78 mmol) in EtOH (20 mL) were refluxed for about 3 hours. The reaction mixture was then cooled to ambient temperature and concentrated in vacuo. The remaining residue was purified by flash chromatography on silica (methanol/ethyl acetate) to yield N-benzyl-5-chloro-3-isopropylpyrazolo[1,5-α]pyrimidin-7-amine as a white solid in analytically pure form (630 mg, 97%).

M.p. 74-75° C. (CHCl$_3$). $^1$H NMR (CDCl$_3$, 300 MHz) δ 7.82 (m, 1H), 7.32 (m, 5H), 7.01 (m, 1H), 5.90 (m, 1H), 4.53 (m, 2H), 3.27 (hep, J=6.9 Hz, 1H), 1.32 (d, J=6.9 Hz, 6H). $^{13}$C NMR (CDCl$_3$, 75 MHz) δ 150.1, 146.8, 144.1, 141.5, 135.7, 129.0, 128.1, 127.1, 116.9, 84.6, 46.0, 23.4, 23.3. IR (neat) $v_{max}$=1617, 1583, 1455, 1168, 740. MS m/z (CI) 301 (M+H), 267, 177, 52. HRMS (CI) Calc.: 301.1220 Found: 301.1230. Microanalysis Calc: C 63.89, H 5.70, N 18.63 Found: C, 63.95; H, 5.78; N, 18.59.

Step 4. Synthesis of tert-Butyl-benzyl-5-chloro-3-isopropylpyrazolo[1,5-α]pyrimidin-7-ylcarbamate

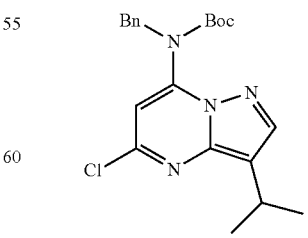

A flask was charged with N-benzyl-5-chloro-3-isopropylpyrazolo[1,5-α]pyrimidin-7-amine (300 mg, 1 mmol), (t-butylOCO)$_2$O (284 mg, 1.3 mmol), DMAP (24 mg, 0.2 mmol)

and THF (6 mL). The mixture was stirred for 1.5 h at rt. Ethyl acetate (10 mL) was added and the organic phase washed with water (3×20 mL), NaHCO$_3$ (20 mL) and dried over Na$_2$SO$_4$. The crude product was purified after concentration by column chromatography on silica (ethyl acetate:hexanes=1:20) to yield the of tert-butyl-benzyl-5-chloro-3-isopropylpyrazolo[1,5-α]pyrimidin-7-ylcarbamate as a pale yellow solid (385 mg, 96%).

M.p. 93-94° C. (ethyl acetate). $^1$H NMR (CDCl$_3$, 300 MHz) δ 8.03 (s, 1H), 7.25 (m, 5H), 6.49 (s, 1H), 5.04 (s, 2H), 3.31 (hep, J=6.8 Hz, 1H), 1.37 (d, J=6.8 Hz, 6H). $^{13}$C NMR (CDCl$_3$, 75 MHz) δ 152.6, 147.9, 144.9, 144.0, 142.5, 136.7, 128.5, 127.7, 127.6, 118.2, 106.1, 82.9, 51.3, 27.8, 23.5, 23.3. IR (neat) ν$_{max}$=2967, 1727, 1612, 1518, 1454, 1154, 699. MS m/z (CI) 401 (M+H), 301, 179, 123, 52. HRMS (CI) Calc.: 401.1744; Found: 401.1747. Microanalysis Calc: C, 62.91; H, 6.29; N, 13.98; Found: C, 62.87; H, 6.19; N, 13.94.

Step 5. Amination of tert-Butyl-benzyl-5-chloro-3-isopropylpyrazolo[1,5-α]pyrimidin-7-ylcarbamate with protected 3-aminobutane-1,2,4-triol Tert-butyl-benzyl-5-chloro-3-isopropylpyrazolo[1,5-α]pyrimidin-7-ylcarbamate and

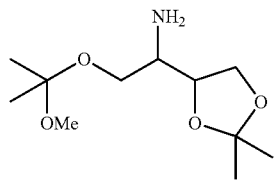 [SMILES: COC(C)(C)OCC(N)C1COC(C)(C)O1]

can be reacted to install an amine group at the 5 position of the tert-butyl-benzyl-5-chloro-3-isopropylpyrazolo[1,5-α]pyrimidin-7-ylcarbamate compound.

The optimum solvent for the reaction is a combination of an ether such as tetrahydrofuran (THF), an alcohol such as methanol (MeOH) and water (H$_2$O) with a tertiary amine such as triethylamine (Et$_3$N) as the base at 30 to 100° C., which allows for a clean substitution reaction with both primary and secondary amines Optimally, a large excess of the base is used and the solvent with base consists of preferably a 1:1:1:1 mixture of triethylamine:tetrahydrofuran:methanol:water. If an excess of the amine nucleophile R$^3$R$^4$NH is used no exogenous base is required. The reactions are optimally carried out at a concentration of 0.5 M with respect to chloride X. The substitution takes between 2 and 24 hours to proceed to competition depending on amine and number of equivalents used. The products are isolated by the addition of water and extraction with ethyl acetate, the excess amine is removed either by distillation or through a wash of the organic phase with aqueous acid solution such as aqueous citric acid.

Step 6. Deprotection to Produce BS-194

The product of step 5 is deprotected under standard conditions to provide the BS-194, which is isolated as the free amine or as a pharmaceutically acceptable salt. It should be noted that any protected side chain functionality may also be deprotected as appropriate. For example, any acid sensitive protecting groups, for example a Boc protecting group, are removed by reaction with an acid such as hydrochloric acid or an equivalent in an aqueous solvent such as aqueous dioxane or methanol to provide BS-194, which is isolated as the free amine or as a pharmaceutically acceptable salt.

Example 3

Synthesis of an Amino Triol Side Chain for the Synthesis of Compounds of Formula I There follows a general description of synthesis of the specified amino triol side chain for the synthesis of the compounds of Formula I. The treatment of an dialkyl D-tartrate such as diethyl D-tartrate with thionyl chloride in a halogenated or hydrocarbon solvent such as dichloromethane or a mixture of a halogenated or hydrocarbon solvent with a a tertiary amine such as triethylamine as base at 0° C. forms the cyclic sulfite. This is used directly in a ring opening reaction with an azide salt such as sodium azide as nucleophile in a dipolar aprotic solvent such as N,N-dimethylformamide (DMF) at 50° C. to form the azido alcohol. Reduction of the diesters with a hydride reductant such as lithium borohydride in an alcohol solvent such ethanol beginning at 0° C. and warming to ambient temperature. Finally the azide is reduced using hydrogen gas most conveniently at one atmosphere pressure catalyzed by a heterogeneous or homogeneous catalyst such as palladium metal supported on carbon in an alcohol solvent such as ethanol most conveniently at ambient temperature.

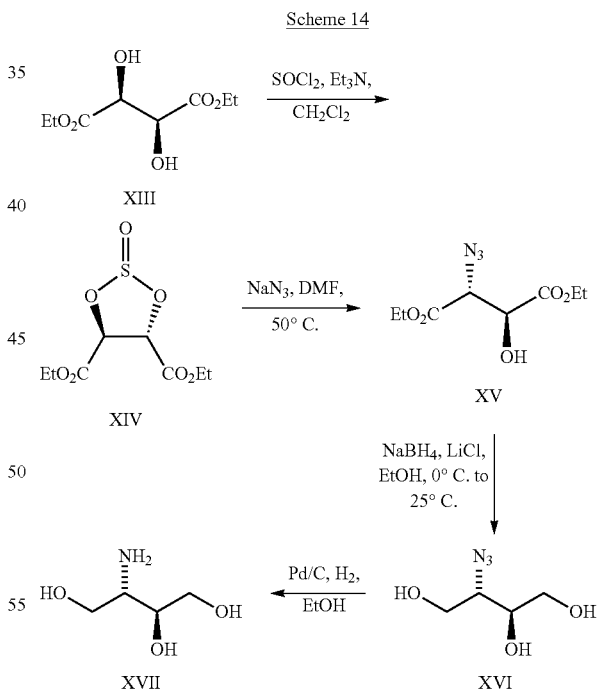

Scheme 14

A protected version of the side chain unit was synthesized using the azido triol intermediate XVII (Scheme 15). This was treated with 2,2-dimethoxypropane with catalysis by an acid such as para-toluenesulfonic acid monohydrate to form double ketal XVIII. Reduction of the azide in XVIII using palladium metal supported on carbon and hydrogen gas afforded the protected amino triol XIX.

Scheme 15

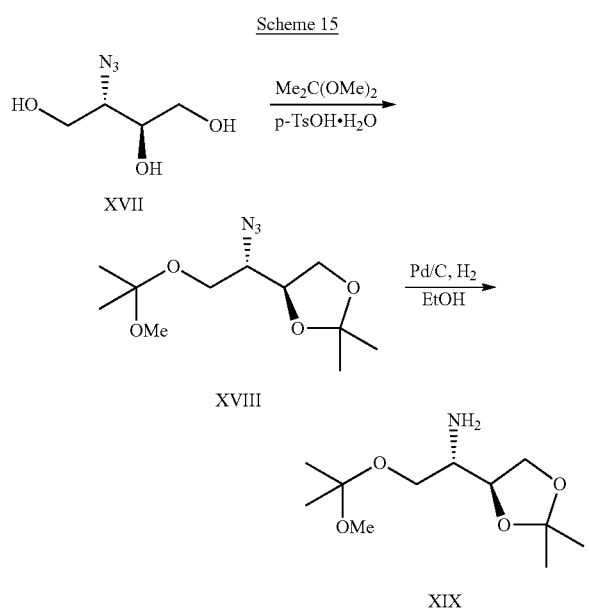

We claim:

1. A process for preparing compounds of Formula I:

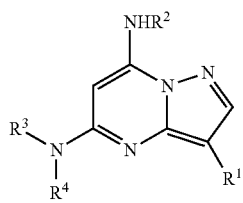

Formula I or salts thereof,
wherein
R¹ is H, halo, alkyl, haloalkyl, cycloalkyl, alkenyl, alkynyl, heterocyclyl, heterocyclylalkyl, aryl, aralkyl, heteroaryl, heteroaralkyl, amino;
R² is alkyl, haloalkyl, cycloalkyl, alkenyl, alkynyl, heterocyclyl, heterocyclylalkyl, aryl, aralkyl, heteroaryl, heteroaralkyl, amino;
R³ is H, alkyl, aryl, cycloalkyl;
R⁴ is alkyl, alkenyl, aryl, arylalkyl, arylalkenyl, cycloalkyl, heterocyclyl, heterocyclylalkyl, heteroaryl, and heteroarylalkyl;
comprising:
(a) reacting a compound of Formula II:

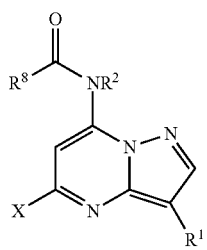

Formula II wherein
R⁸ is $C_{1-8}$ alkyl, $C_{6-14}$ aryl, $C_{7-20}$ arylalkyl, $C_{4-7}$ heterocyclic, $C_{5-15}$ heterocyclicalkyl, $C_{4-7}$ heteroaryl, $C_{5-15}$ heteroaralkyl, $C_{1-8}$ alkoxy, $C_{6-14}$ aryloxy, $C_{7-20}$ arylalkoxy, $C_{4-7}$ heterocyclicoxy, $C_{5-15}$ heterocyclicalkoxy, $C_{4-7}$ heteroaryloxy, or $C_{5-15}$ heteroaralkyloxy;
X is F, Cl, Br, or I;
R¹ is as defined above; and
R² is as defined above and is, optionally, protected with a protecting group;
with a compound of Formula III:

$$R^3R^4NH \quad\quad \text{Formula III}$$

wherein
R³ is as defined above and is, optionally, protected with a protecting group;
R⁴ is as defined above and is, optionally, protected with a protecting group;
in a solvent system comprising water and one or more organic solvents, optionally in the presence of a base; and
(b) deprotecting the resulting compound to produce a compound of Formula I or a salt thereof;
wherein each alkyl group may be optionally substituted by one or more halo, alkyl, lower alkyl, alkenyl, cycloalkyl, acyl, hydroxy, hydroxyalkyl, heterocyclic, heteroaryl, aryl, amino, aminoalkyl, —NR$^x$R$^y$, oxo, cyano, carboxy, carboxyalkyl, alkoxycarbonyl, —OR$^x$, —C(O)R$^x$, —C(O)—NH$_2$, —C(O)—N(H)R$^x$, —C(O)—N(H)O R$^x$, —C(O)—NR$^x$R$^y$, —NR$^y$C(O)R$^x$, —NR$^y$C(O) NR$^x$R$^y$, —OC(O)NR$^x$R$^y$, —NR$^y$C(O)OR$^x$, —S(O)$_n$— R$^x$, —S(O)$_2$—NH$_2$, —S(O)$_n$—N(H)R$^x$ and/or —S(O)$_2$—NR$^x$R$^y$, wherein R$^x$ and R$^y$ are each independently $C_{1-6}$ alkyl.

2. The process of claim 1, wherein step (a) occurs below 100° C.

3. The process of claim 1, wherein step (a) proceeds to completion in less than 24 hours.

4. The process of claim 1, wherein step (a) proceeds in the absence of a transition metal catalyst.

5. The process of claim 1, wherein the solvent system comprises two or more organic solvents and water.

6. The process of claim 1, wherein the solvent system comprises an ether, an alcohol and water.

7. The process of claim 1, wherein the solvent system comprises tetrahydrofuran, methanol and water.

8. The process of claim1, wherein the solvent system comprises a base.

9. The process of claim 1, wherein step (a) comprises an excess of the compound of Formula III.

10. The process of claim 1, wherein the compound of Formula I is a compound of Formula V or salts or a diastereomer thereof:

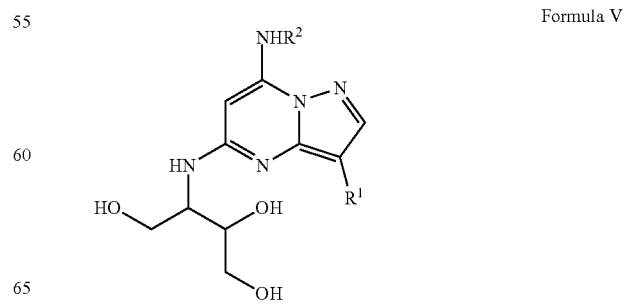

Formula V wherein:

R[1] is H, $C_{1-5}$ alkyl or halo-substituted $C_{1-5}$ alkyl;

R[2] is substituted or unsubstituted $C_{1-8}$ alkyl, $C_{7-12}$ aralkyl, or $C_{5-20}$ heteroaralkyl.

11. The process of claim 1, wherein the compound of Formula III is a compound of Formula VI

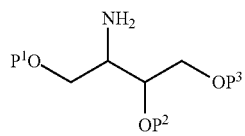

Formula VI wherein:

P[1], P[2] and P[3] are each a hydroxy protecting group that is cleaved under acidic conditions.

12. The process of claim 10, wherein the compound of Formula V is selected from the groups consisting of:

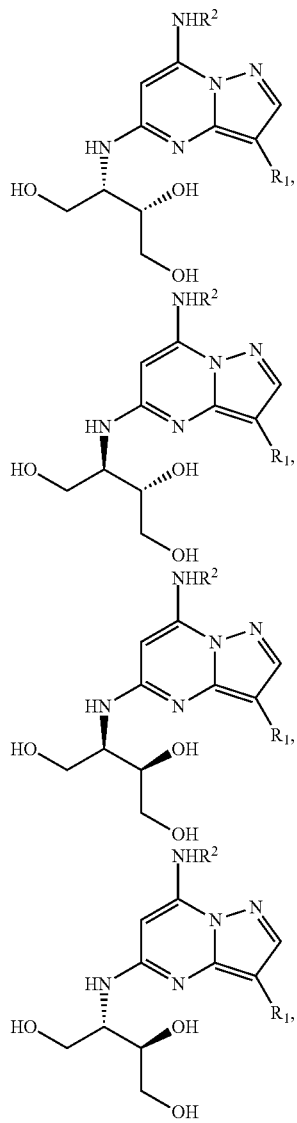

a mixture of diastereomers of

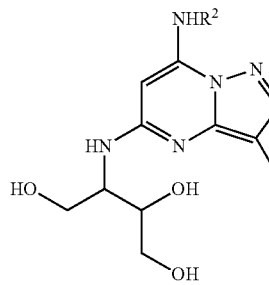

, and salts thereof.

13. The process of claim 10, wherein the compound of Formula V is selected from the groups consisting of:

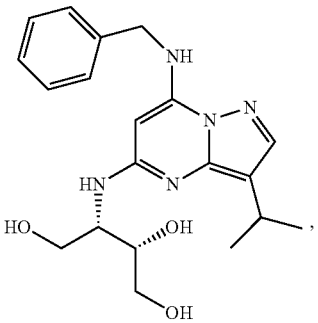

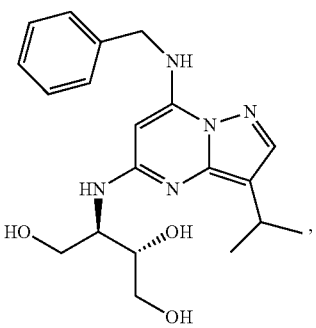

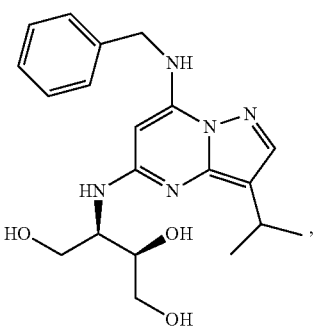

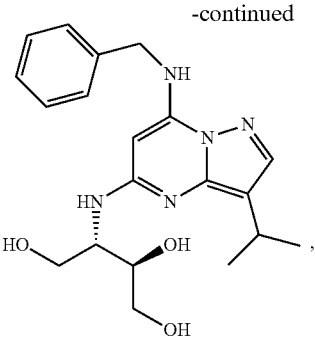
a mixture of diastereomers of
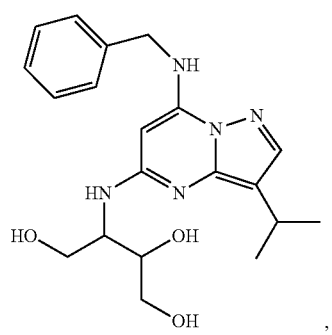, and salts thereof.
* * * * *